United States Patent [19]

Chamoun

[11] Patent Number: 5,010,891
[45] Date of Patent: Apr. 30, 1991

[54] CEREBRAL BIOPOTENTIAL ANALYSIS SYSTEM AND METHOD

[75] Inventor: Nassib G. Chamoun, Dedham, Mass.

[73] Assignee: Biometrak Corporation, Cambridge, Mass.

[21] Appl. No.: 336,874

[22] Filed: Apr. 12, 1989

Related U.S. Application Data

[63] Continuation-in-part of Ser. No. 107,357, Oct. 9, 1987, Pat. No. 4,907,597.

[51] Int. Cl.$^5$ ............................................. A61B 5/04
[52] U.S. Cl. .................................................... 128/731
[58] Field of Search .................. 128/731, 732, 733; 364/413.02

[56] References Cited

U.S. PATENT DOCUMENTS

| | | | |
|---|---|---|---|
| 4,407,299 | 10/1983 | Culver | 128/732 |
| 4,697,598 | 10/1987 | Bernard et al. | 128/731 |
| 4,753,246 | 6/1988 | Freeman | 128/731 |

OTHER PUBLICATIONS

Withington, P. S., Morton, J., Arnold, R., Sebel, P.S., and Moberg, R., Assessment of Power Spectral Edge for Monitoring Depth of Anesthesia using Low Methohexitone Infusion. Int-J-Clin-Monit-Computing. 3(2): pp. 117-122 (1986).

Levy, W. J., Intraoperative EEG Patterns: Implications for ERG Monitoring. Anesthesiology. 60(5): pp. 430-434 (1984).

(List continued on next page.)

*Primary Examiner*—Francis Jaworski
*Assistant Examiner*—George Manuel
*Attorney, Agent, or Firm*—Hale and Dorr

[57] ABSTRACT

Disclosed is a real time cerebral diagnostic apparatus and method for quantitatively evaluating, in a noninvasive manner, cerebral phenomena such as the depth and adequacy of anesthesia pain responses during surgical stress, acute cerebral ischemia, level of consciousness, degree of intoxication and ongoing normal and abnormal cognitive processes. A suitable electrode and amplifier system is used to obtain high resolution biopotentials from the regions of interest. Surface electroencephalographic (EEG) signals are filtered to allow the acquisition of frequencies between 2 and 500 Hz, then digitized and transmitted over a high speed serial line to a host computer where a 32 second long signal is divided into 128 consecutive 0.25 second intervals. Digital EEG data from unipolar leads is normalized and the dynamic phase and density relations within the signal are then characterized by estimating the third-order autocorrelation function or autobispectrum using either a frequency domain, or parametric approach. Paired EEG data from corresponding left and right hemisphere leads is used to characterize the dynamic phase and density relations between hemispheres by estimating the third order crosscorrelation function or crossbispectrum using either frequency domain or parametric techniques. Under certain specific filtering circumstances the power spectrum and crosspower spectrum are also computed. A reference clinical database is used to identify frequency pairs most sensitive to particular interventions or diagnostic states of interest. The values at these frequency pairs are then extracted from the patient's autobicoherence, autobispectral density, autobiphase, crossbicoherence, crossbispectral density, and crossbiphase arrays. The ensemble of values for the particular diagnostic determination is used to compute an index which serves as the diagnostic criterion by which the patient's state is judged. Any diagnostic index can be continuously displayed on a graphics terminal for real-time diagnostic monitoring or can be sent to a hard copy device to generate reports for the medical record.

70 Claims, 18 Drawing Sheets

OTHER PUBLICATIONS

Pichlmayr, I., and Lips, U., EEG Monitoring in Anesthesiology and Intensive Care. Neuropsychobiology. 10(4): pp. 239–248 (1983).

Baker, A. B., and Roxburgh, A. J., Computerised EEG Monitoring for Carotid Endarterectomy. Anaesth-Intensive Care (14(1): pp. 32–36 (1986).

Brillinger, D. R., An Introduction to Polyspectra. Annals of Mathematical Statistics 36:1351–1374 (1965).

Russ, W., Kling, D., Krumholz, W., Fraedrich, G., and Hempelmann, G., [Experience with a New EEG Spectral Analyzer in Carotid Surgery] Erfahrungen mit einem neuen EEG-Spektralanalysator in der Karotischirurgie. Anaesthetist 45(2): pp. 85–90 (1985).

Rampil, I. J., Holzer, J. A., Quest, D. O., Rosenbaum, S. H., and Correll, J. W., Prognostic Value of Computerized EEG Analysis during Carotic Endarterectomy. Anesthesia Analgesia 62:186–192 (1983).

Huber, P. J., B. Kleiner, T. Gasser and G. Dumermuth. Statistical Method for Investigating Phase Relations in Stationary Stochastic Processes. IEEE Trans. Aud. and Electroacou. AU-19/1:78–86 (1971).

Tryon, P. V., The Bispectrum and Higher-Order Spectra: A Bibliography. U.S. NBS (Tech Note 1036) (1981).

Nikias, C. L., and Raghuveer, M. R., Bispectrum Estimation: A Digital Signal Processing Framework, Proc. IEEE, 75,7:869–891 (1987).

Susumu, T., and Osamu, T., Analysis of Wave Shapes of Alpha Waves on EEG by Means of the Bispectrum. (1973).

Kleiner, B., Huber, P. J., and Dumermuth, G., Analysis of the Interelations Between Frequency Bands of the EEG by Means of the Bispectrum. Electroencephalogr. Neurophysiol. 27(7): 693–694 (1969).

Dumermuth, G., Huber, P. J., Kleiner, B., and Gasser, T., Analysis of the Interrelations Between Frequency Bands of the EEG by Means of the Bispectrum. A preliminary Study. Electroencephalogr. Clin. Neurophysiol. 31(2):137–148 (1971).

Barnett, T. P., Johnson, L. C., Naitoh, P., Hicks, N. and Nute, C., Bispectrum Analysis of Electroencephalogram Signals During Waking and Sleeping. Science 172:402–401 (1971).

Raghuveer, M. R. and Nikias, C. L. Bispectrum Estimation: A Parametric Approach. IEEE Trans. on Acoustics, Speech & Signal Processing. 33:1213–1230 (1985).

Volavka, J., Matousek, M., Feldstein, S. et al., The Reliability of Electroencephalography Assesement. Electroencephalography and Electromyography. 4:123 (1973).

Eichhorn, J. H., Cooper, J. B., Cullen, D. J., Ward, M. R., Philip, J. H., and Seeman, R. G., Standards for Patient Monitoring During Anesthesia at Harvard Medical School. JAMA. 256(*): pp. 1017–1020 (1986).

Jasper, H. H., The Ten-Twenty Electrode System of the International Federation in Electroencephalography and Clinical Neurophysiology. EEG Journal. 10:371–375 (1985).

Haykin, S., Adaptive Filter Theory. Prentice-Hall, Englewood Cliffs, N.J. (1986).

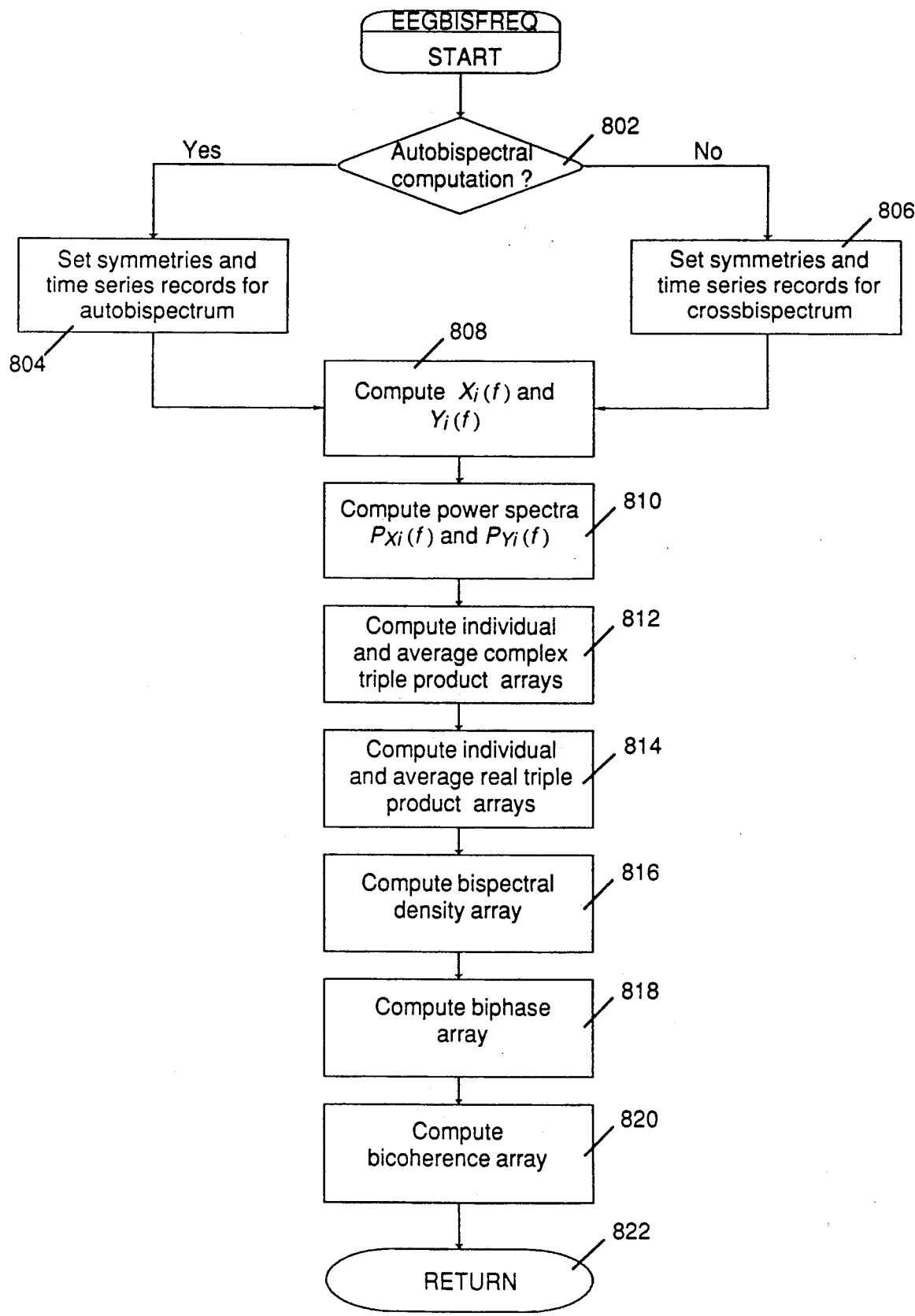

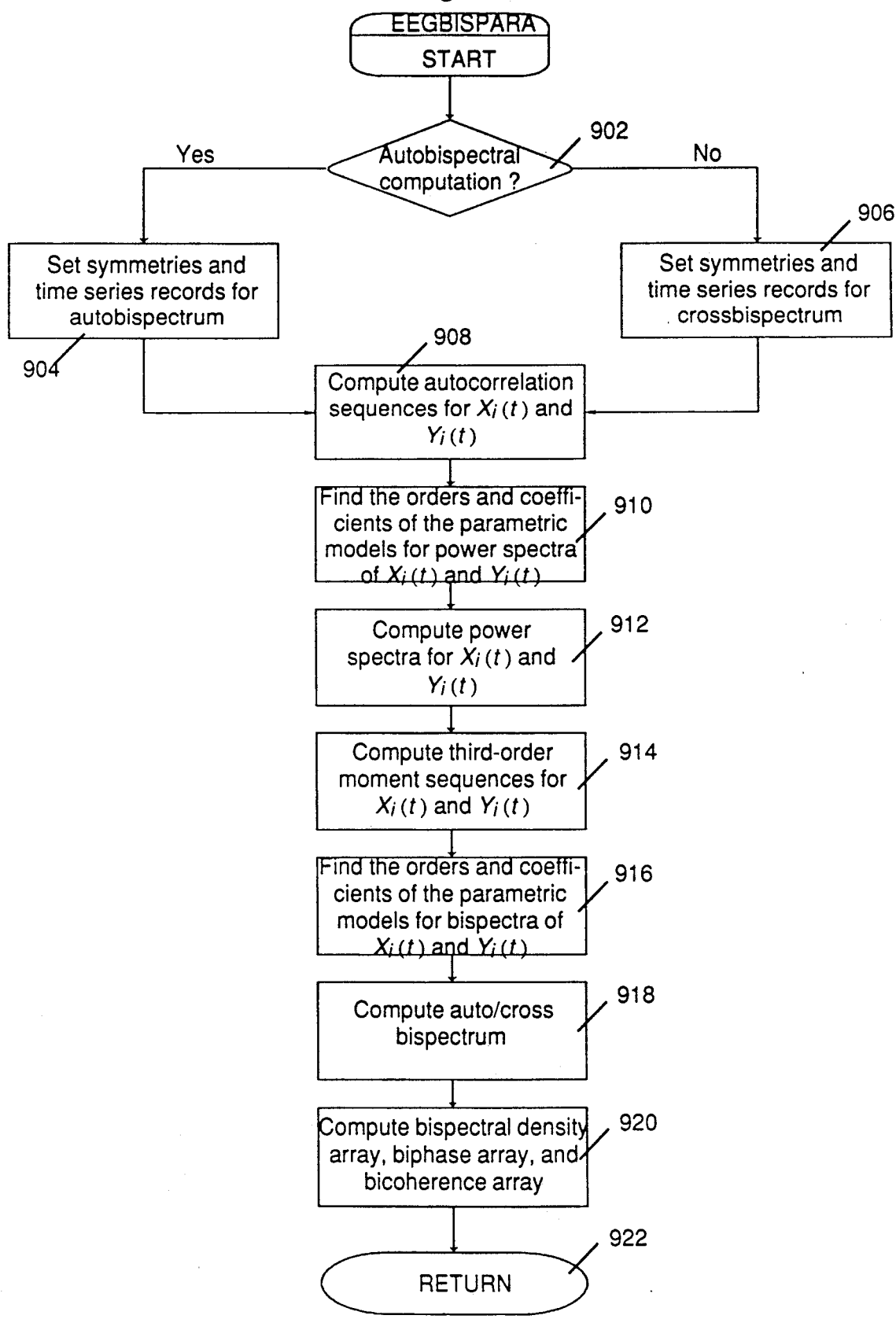

Bispectral Density During Control

Bispectral Density During Deep Anesthesia

Bispectral Density During Recovery

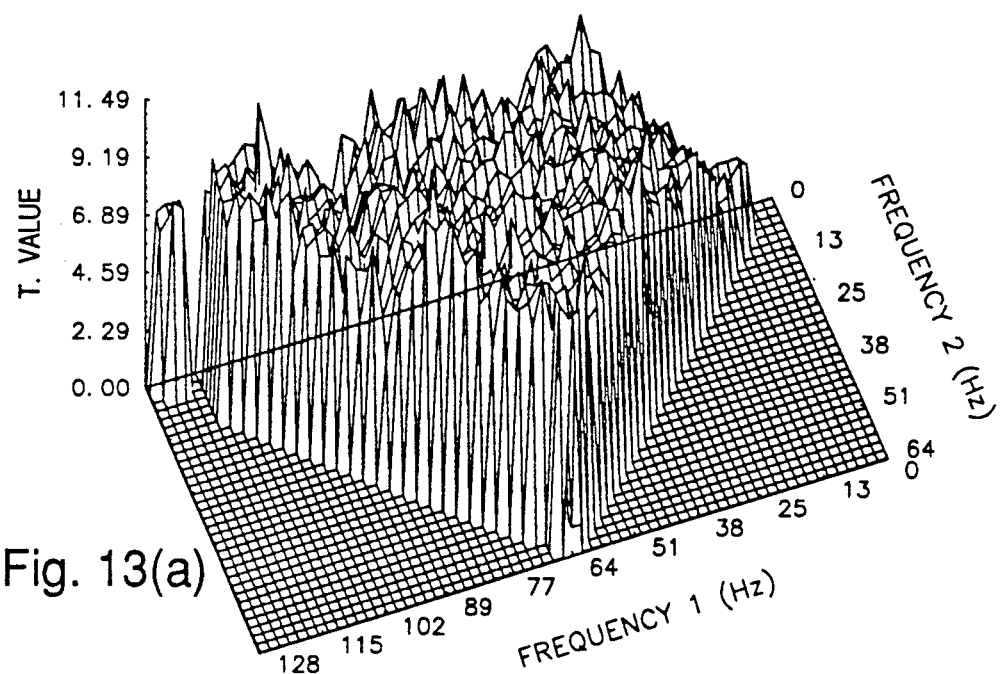
T. Array Showing ALL Data Points
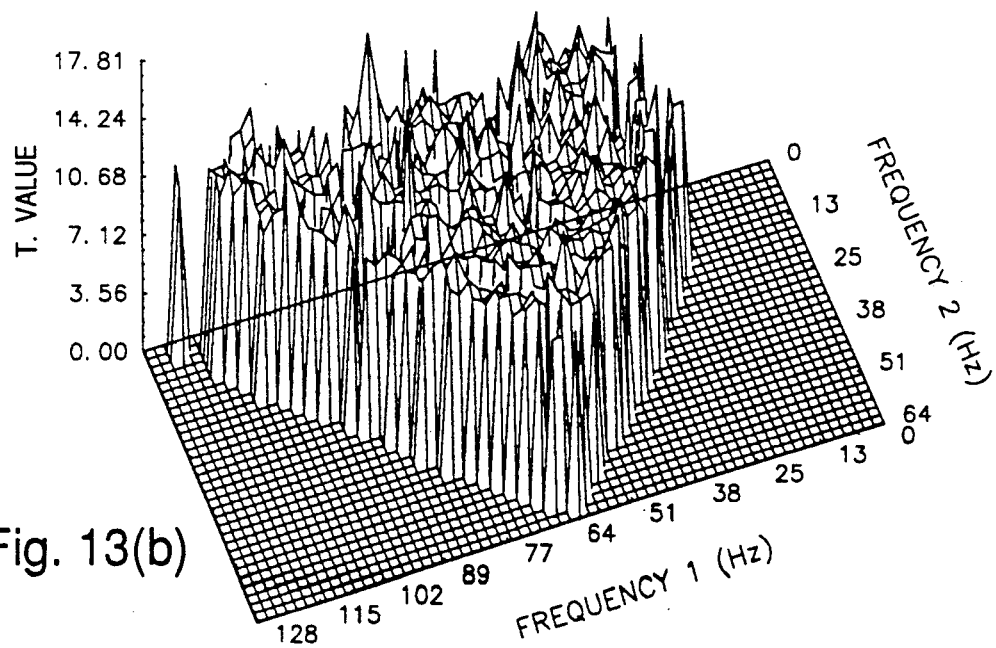
T. Array Showing Only Data Points Above 10.0

CEREBRAL BIOPOTENTIAL ANALYSIS SYSTEM AND METHOD

This application is a continuation-in-part application of co-pending U.S. Ser. No. 107,357 filed Oct. 9, 1987, now U.S. Pat. No. 4,907,597 which is also assigned to the assignee of the present application.

BACKGROUND OF THE INVENTION

The present invention relates to a real-time, high-frequency, high-resolution cerebral biopotential analysis system and method, and more particularly to a computer-based biopotential diagnostic system and method for quantitatively determining, in a noninvasive manner, cerebral phenomena that can be ascertained by analyzing cerebral electrical activity.

Despite a considerable expenditure of time and effort, current approaches to the quantitative, noninvasive assessment of cerebral electrical activity, as displayed in an "EEG" waveform, have not been successful in fully extracting all of the information which is present in this complex waveform. A great need remains for an accurate, sensitive, reliable, and practical neurologic profiling technology. In particular, contemporary intra-operative EEG monitoring techniques have not been widely adopted due to their inherent limitations. Indeed eighty percent (80%) of all medical malpractice suits are believed to be related to post-anesthesia morbidity and mortality, and if such EEG monitoring techniques were reliable they certainly would have been adopted.

A number of devices known in the prior art are capable of tracking cerebral activity qualitatively. Techniques involving the use of the "classical", conventional analog EEG are restricted to analyses in the time domain, and require considerable training for adequate interpretation. Moreover, since the frequency resolution of the human eye at standard speeds and gain is 30-60 Hz, much high frequency content is invisible. Thus visual EEG assessment is better characterized as being an art rather than a science. In fact, it has been shown that the average correlation between seven experienced readers did not exceed 56 per cent.

The use of frequency (power spectrum) analysis of the EEG in the 1960's introduced the notion of some basic processing of the signal prior to visual inspection and led to the application of frequency analysis of the EEG to various cerebral monitoring problems. In the past 25 years at least 100 papers have been published in the medical literature describing applications of power spectral analysis for purposes such as assessing the depth of anesthesia and cerebral ischemia under various intraoperative conditions. U.S. Pat. No. 4,557,270 issued to John also describes the use of power spectral analysis to evaluate cerebral perfusion during open heart surgery. Several recent studies, however, have shown many deficiencies in the use of power spectral analysis to monitor cerebral perfusion and to determine post operative neurologic outcome. In addition, neither power spectral analysis nor any other monitoring technique has been shown to be reliable, and this is demonstrated by the fact that the well-accepted Harvard Medical School Anesthesia Monitoring Standard does not include any type of intraoperative neurologic monitoring due, in all likelihood, to the complexity of interpreting raw EEG data and the unreliability of existing automated systems utilizing power spectral or time-domain analytic techniques.

The discharge of thousands of bio-electrically active cells in the brain, organized in larger, interacting neural centers contributes to the formation of an electrical signal with a wide frequency spectrum and extremely complex dynamics. Embedded in that signal is information regarding frequency content, non-linearities, and phase relationships arising from the complex neuronal firing patterns that take place. Because of the complexity of the EEG signal, conventional time and frequency modes of analysis have not been adequate t fully profile its behavior. In the Fourier transform of the second order autocorrelation function (the power spectrum) processes are represented as a linear summation of statistically uncorrelated sine-shaped wave components. Contemporary approaches to monitoring the EEG by means of the power spectrum have thus suppressed information regarding non-linearities and inter-frequency phase relationships and are of limited utility in representing the EEG's dynamic structure. Furthermore the high frequency low amplitude elements of the EEG have been discarded to date by the filtering and sampling characteristics of known analysis techniques.

Because the EEG has a wide spectrum and is highly dynamic and non-linear, the phase relationships within the EEG, especially in the higher frequencies, must carry a great deal of diagnostic information regarding cerebral function. The Fourier transform of the third order autocorrelation function, or autobispectrum, is an analytic process that quantifies deviation from normality, quadratic non-linearities and inter-frequency phase relationships within a signal. The Fourier transform of the third order crosscorrelation function, or crossbispectrum, is an analytic process that provides similar information between two signals.

Autobispectral analytic techniques have been applied to the EEG signal and the basic bispectral properties of the conventional EEG focusing o frequencies below 32 Hz have been investigated. Such studies have also been conducted to search for changes between waking and sleeping by means of autobispectral analysis. Autobispectral analysis and power spectral analysis have also been used in an attempt to show that the EEGs of monozygotic twins are similar in structure.

To date, no previous study has examined the high frequency (greater than 32 Hz) content of the EEG and found information of diagnostic value. It also does not appear that any study has shown autobispectral or crossbispectral analysis to be of any value for any diagnostic purpose and certainly neither of these analytic techniques have been shown to have any value in quantifying depth and adequacy of anesthesia, pain responses induced by surgical stress, cerebral ischemia, consciousness, degrees of intoxication, ongoing cognitive processes or interhemispheric dynamic phase relations.

It is therefore a principal object of the present invention to provide a noninvasive high resolution high frequency electroencephalographic system and method capable of recognizing and monitoring physical phenomena that are reflected in cerebral electrical activity.

Another object of the present invention is to provide a noninvasive electroencephalographic system and method capable of determining and monitoring depth and adequacy of anesthesia, pain responses during surgical stress, acute cerebral ischemia, level of consciousness, degrees of intoxication and normal or abnormal cognitive processes.

Accordingly, the system and method of the present invention utilizes a suitable electrode and amplifier system to obtain 19 unipolar EEG signals from regions of interest on both left and right hemispheres of a subject's brain. Band-pass filtering of 2–500 Hz is used to obtain signals with a high frequency content. High gain amplifiers maximize the dynamic range for the high frequency, low energy wave components of the signals. The system applies digital sampling techniques to the signals and transmits digitized data over a high speed serial line to a host computer. The system divides a 32 second long data segment from each lead into 128 consecutive 0.25 second intervals. The system normalizes all 19 unipolar leads by the standard deviation, and then characterizes the dynamic phase relations within the signal by processing for autobispectral variables using either a Fast Fourier Transform (FFT) based approach, or a parametric cubic fitting approach. Similarly three corresponding left and right hemisphere data pairs are normalized in the same manner and dynamic phase relations between two hemispheres are then characterized by processing for crossbispectral estimates utilizing either the FFT or parametric based techniques. The outcome is a set of two dimensional arrays representing the dynamic interactions between all the possible combinations of frequencies (frequency pairs) in the spectrum of interest. For each unipolar lead, three arrays are produced: autobicoherence, autobispectral density and autobiphase. Three arrays are also generated for each bipolar data set: crossbicoherence, crossbispectral density and crossbiphase.

Each of the autobispectral and crossbispectral arrays contains 16,512 data points. Although all, or nearly all, of these values can be expected to change from normal during different interventions or due to differing disease states, in the preferred embodiment only those points which show the greatest fidelity in tracking the particular diagnostic determination in question are utilized to create a diagnostic criterion. The ensemble of points most sensitive to a particular intervention or ongoing physiologic process can be used to create a clinically useful single-number index from the computed bispectral arrays. The system uses these indices as a diagnostic figure of merit for the assessment of depth and adequacy of anesthesia, pain responses during surgical stress, acute cerebral ischemia, level of consciousness, degree of intoxication and normal or abnormal cognitive processes. This approach makes it possible for any, even unskilled, operator to meaningfully interpret the output of the diagnostic device.

In situations where continuous monitoring is required, indices can be continuously displayed on a video terminal thereby enabling the operator to interactively evaluate regions of interest. For record keeping purposes index values and other pertinent variables can be sent to a hard copy output device or stored on a disk.

These and other objects and features of the present invention will be more fully understood from the following detailed description which should be read in light of the accompanying drawings in which corresponding reference numerals refer to corresponding parts throughout the several views.

BRIEF DESCRIPTION OF DRAWINGS

FIG. 8 is a flow chart of frequency domain based method for producing autobispectrum or crossbispectrum used by the system of FIG. 1;

FIG. 9 is a flow chart of a parametric based method for producing autobispectrum or crossbispectrum in the system of FIG. 1.

FIG. 10($b$) is an illustration of a graph showing a biphase array generated by the system of FIG. 1;

FIG. 10($c$) is an illustration of a graph showing a bicoherence array generated by the system of FIG. 1;

FIGS. 13($a$)–13($b$) are graphs of statistical arrays generated by the system and method of the present invention;

DETAILED DESCRIPTION OF THE PREFERRED EMBODIMENTS

Figure 1:
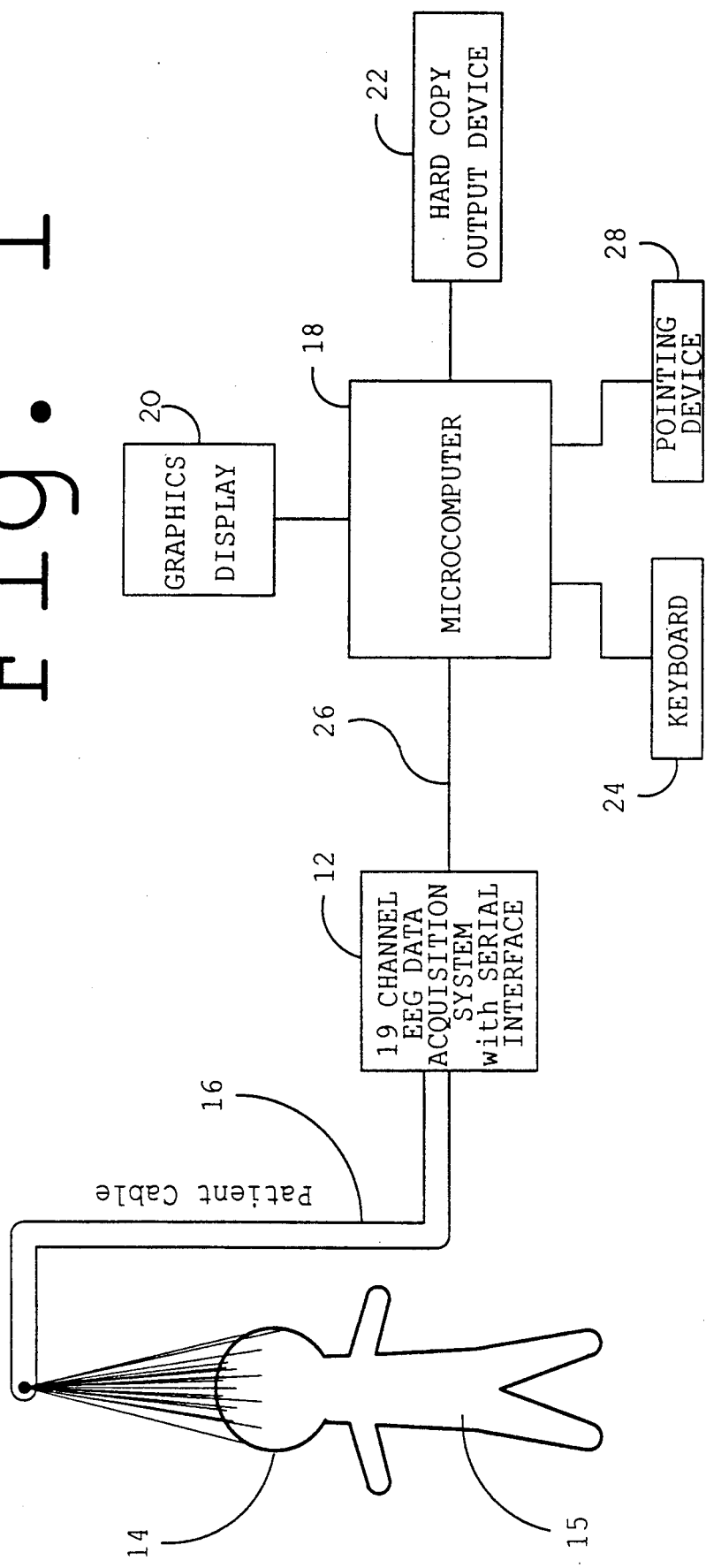
FIG. 1 is a schematic view of the system of the present invention for detecting cerebral phenomena in a noninvasive manner.

Referring to FIG. 1 the apparatus of the present invention includes a 19 channel EEG data acquisition system 12 connected to a microcomputer 18 through a high speed serial interface 26.

The EEG leads are connected to a patient's head 14 by a set of surface elctrodes. The International 10/20 electrode system and nomenclature is preferred. The EEG signals are picked up by the electrodes and transmitted over a patient cable 16 to the EEG data acquisition system 12.

The data acquisition system 12 filters, amplifies and digitizes the EEG waveforms and sends the digitized data to the microcomputer 18 via a high speed synchronous serial line 26. In addition, the serial line 26 can be used to download filtering, gain and sampling rate instructions to the data acquisition unit 12.

The microcomputer 18 processes the serial data stream in order to generate all computed data arrays. These arrays are then used in conjunction with predetermined reference arrays derived from clinical studies to produce diagnostic indices which indicate the status of the patient. These indices are displayed on the graphics display 20. Printed output of the diagnostic index is also available on the hard copy output device 22 which is connected to the microcomputer 18. Interaction between the operator and the acquisition and analysis components of the system is provided by means of a keyboard 24 and pointing device 28 with feedback on the graphics display 20.

Figure 2:
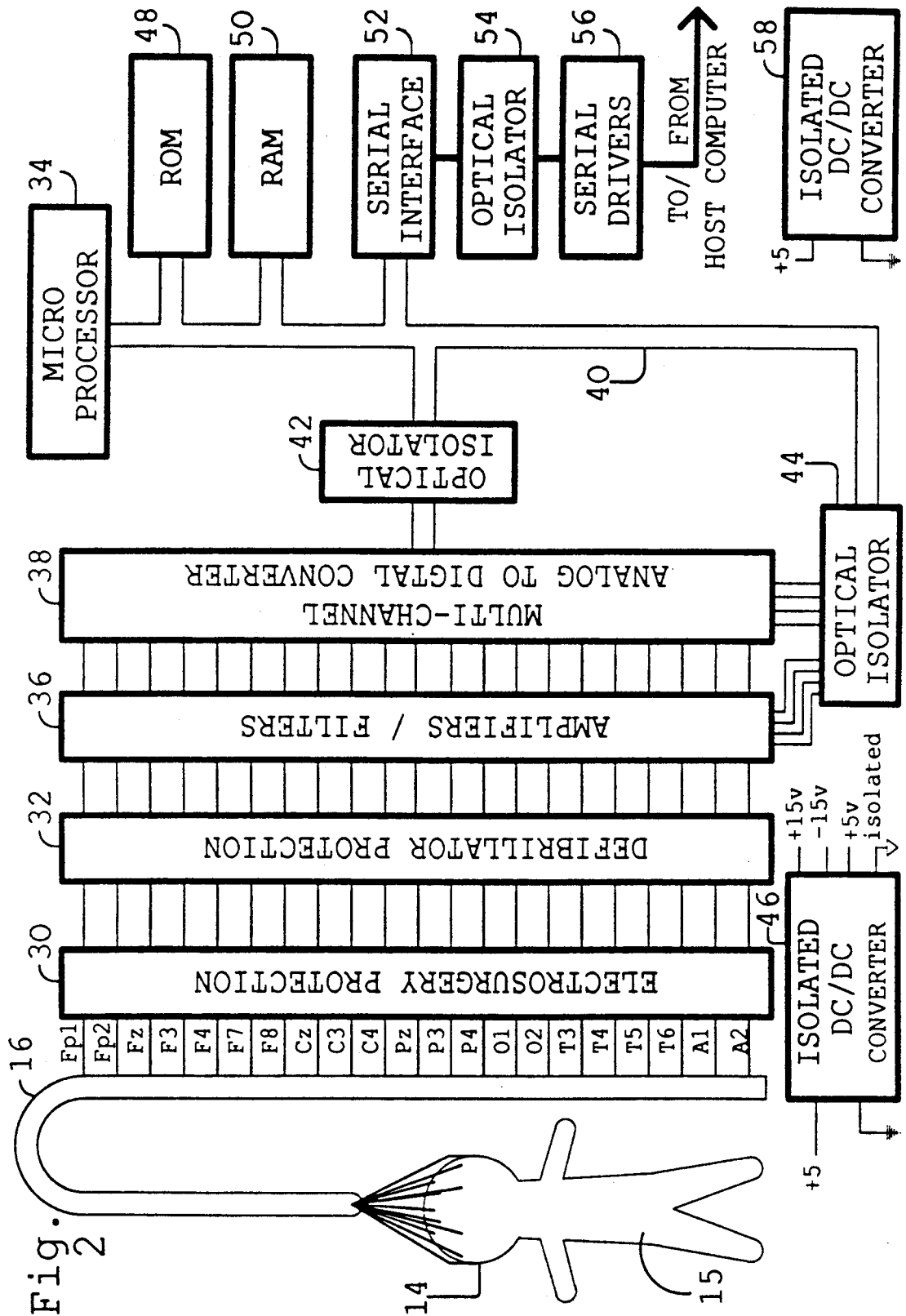
FIG. 2 is a schematic view of a 19 channel EEG data acquisition system including a serial interface utilized in the system of FIG. 1.

The 19 channel data acquisition system 12 is shown in greater detail in FIG. 2. The EEG surface potential, detected by a surface electrode mounted on the patient head 14, passes through an electrosurgery protection circuit 30, a defibrillator protection circuit 32, and an amplifier/ filter circuit 36 before being passed on to the multi-channel analog to digital converter 38.

The electrosurgery protection circuit 30 includes a radio frequency (rf) filter, which limits the rf current through the patient leads 16 to less than 100 microamperes and thus protects the patient 15 from rf burns and protects the amplifiers 36 from damage resulting from exceeding the absolute maximum input voltage specified by the manufacturer. This circuit can be an LC section circuit consisting of a generic inductor connected in series to a generic capacitor which is then connected to ground.

The defibrillator protection circuit 32 limits the voltage to the amplifiers 36 to a safe level when a defibrillator is applied to the patient 15 and discharged. This circuit can consist of a neon light bulb and or a parallel variable resistor connected in series to a grounded resistor.

The amplifier/ filter circuitry 36 is controlled by the microprocessor 34 for default gain and filtering levels or alternate gain and filtering levels as requested by the operator. Preferred gain and filtering settings are discussed later. This circuit section consists of three stages; the first is a pre-amplifier stage that can be assembled using a wide variety of high impedance pre-amplifiers such as those sold by National Semiconductor, Sunnyvale CA; the second is a programmable filters stage which can utilize components from Frequency Devices, Haverhill MA; the third stage is a programmable amplifiers stage which can be assembled from operational amplifiers used in conjunction with a multiplying digital to analog (D/A) converter both components can be supplied by National Semiconductor. The multiplying D/A is used to set the gain to the appropriate levels requested by the microprocessor 34.

The high impedance pre-amplifier of each channel will saturate to either the positive or negative supply voltage if the input of the pre-amplifier is not terminated. This will lead to large positive value or a large negative value at the output of amplifier/ filter section 36. Such values will be used to identify lead failure.

The output of all 19 channels of the amplifier/ filter 36 is fed to a multi-channel analog to digital converter (A/D) 38 which is under microprocessor 34 control for sampling rate settings. The analog signals are converted to digital data format suitable for input to a computer. A/D converters sold by Analog Devices, Norwood MA can be used for this purpose.

The multi-channel A/D converter 38 is optically coupled to data bus 40 by optical isolator 42. All control lines to the sample and hold circuits, the multiplexer and the A/D convertor 38 are also optically isolated by optical isolator 44. Any known optical isolators can be used for this purpose.

All DC power lines going to the amplifiers 36, sample and hold circuits, multiplexer and A/D convertor 38 are also isolated from the AC power line with a DC/DC convertor 46 in order to provide complete patient isolation from ground. DC/DC converters available from Burr Brown can be used for this purpose.

The basic instructions for controlling operation of the microprocessor 34 are stored in a read only memory (ROM) 48. The random access memory (RAM) 50 is used as a buffer memory for data and a portion of the RAM 50 can also be used as program memory when a control program is being downloaded from the microcomputer 18.

Serial interface 52 operates under the control of the microprocessor 34. The serial interface 52 is optically coupled with optical isolators 54 to high speed synchronous serial drivers 56 to provide a synchronous serial link between the 20 channel data acquisition system 12 and any compatible high speed synchronous serial interface card on any computer. The serial lines are isolated by optical isolators 54 and DC/DC convertor 58 to provide increased patient safety and to protect the host computer 18 from any transients.

Figure 3:
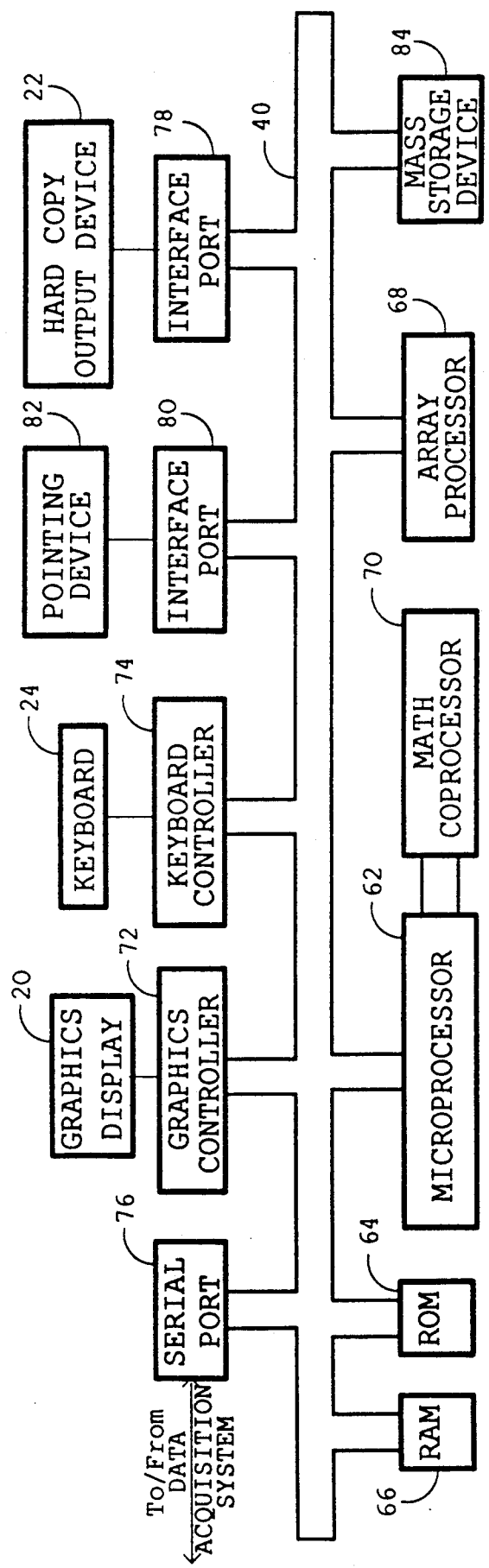
FIG. 3 is a schematic view of the microcomputer used to calculate and display the EEG bispectrum in the system of FIG. 1.

The host or microcomputer 18 of FIG. 1 is shown in greater detail in FIG. 3. The entire microcomputer system runs under control of a microprocessor 62 with the program memory for the microprocessor 62 being stored in ROM 64. The RAM 66 is used for storage of intermediate data. The mass storage device 84 is used for storing clinical databases as well as archiving patient data.

In a preferred embodiment, the microcomputer 18 contains an array processor 68 (such as the Vortex sold by SKY of Lowell, MA) on which complex arithmetic calculations can be performed on entire arrays of data simultaneously. The preferred embodiment also includes a math coprocessor 70 which is connected directly to microprocessor 62. The math coprocessor 70 is used for scalar and graphic calculations while the array processor 68 is used to calculate bispectral and other data vectors.

A graphics controller 72 operating under program control of the microprocessor 62 drives a graphics display 20. A keyboard controller 74 interfaces directly with the operator's keyboard 24. A serial port 80 interfaces with a pointing device 82.

Operator control of the entire acquisition, analysis and display procedure is controlled by the keyboard 24 and pointing device 82 with feedback on the graphics display 20. One high speed synchronous serial port 76 is provided to interface with the 20 channel data acquisition system 12. Port 76 can be used to send control data to the system (e.g., filtering, gain, sampling rate, start/ stop acquisition, perform self diagnostics) and to receive EEG data from the system, as well as to download program data to the system. Another serial or parallel port 78 is provided to drive a hard copy output device 22 for printing desired diagnostic indices.

Figure 4:
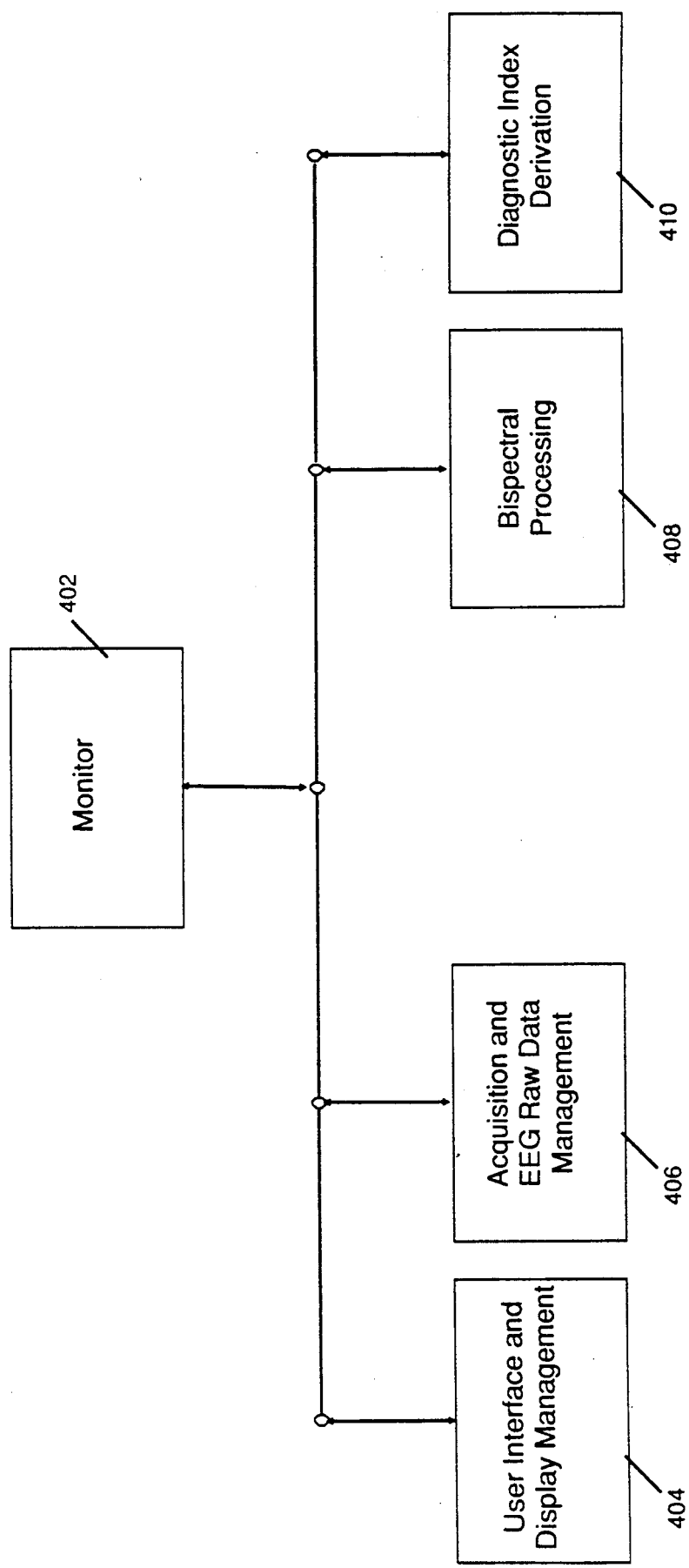
FIG. 4 is a schematic view of the processing operations performed by the system of FIG. 1

Referring now to FIG. 4, a block diagram of the system operations and the method of the present invention is described. As mentioned above, the system and method of the present invention computes dynamic phase and density relations of EEG signals from a preselected number of leads (19 unipolar and 6 bipolar in the described embodiment). Single number diagnostic indices are then generated from the data arrays by utilizing predetermined reference arrays. The results are quantitative indices useful for analyzing cerebral electrical activity as it relates to, for example, the assessment of depth and adequacy of anesthesia, pain responses during surgical stress, acute and chronic cerebral ischemia, level of consciousness, degree of cerebral intoxication and normal or abnormal cognitive processes.

The monitor module 402, handles the overall operations of the system via integration of data and process information from the user interface module 404, acquisition and raw EEG data management module 406, bispectral processing module 408 and diagnostic index derivation module 410. A detailed illustration of module 402 can be found in FIG. 5.

The user interface and display management module 404 represents the means through which the operator controls and interacts with the system during the course of a procedure. This includes, but is not limited to, entry of information regarding the patient, type of diagnostic procedure being carried out, lead and acquisition settings; continuous display of acquisition status, lead integrity, and diagnostic indices corresponding to regions probed by each electrode; and requests for printing and archiving results to disk. Module 404 directly interacts with the monitor module 402. The operations handled by module 404 can be achieved under one of many commercially available environments such as Microsoft's Windows.

The acquisition and raw EEG data management module 406, handles all of the raw EEG data checking and processing prior to bispectral analysis. This includes, but is not limited to, continuous acquisition of EEG data and the verification of the integrity of the data; preparing all unipolar EEG data for autobispectral processing; preparing all bipolar EEG data for crossbispectral processing. Module 406 directly interacts with the monitor module 402. A more detailed description of module 406 is provided below in connection with FIG. 7.

The bispectral processing module 408 controls the generation of all data arrays measuring dynamic phase and density relations within the EEG. This information can be organized in both autobispectral and crossbispectral arrays utilizing either an FFT based or parametric based approach. The tasks performed by this module include, but are not limited to: Fourier transformation; and the generation of power spectrum, autobispectral density, crossbispectral density, autobicoherence, crossbicoherence, autobiphase, and crossbiphase. Module 408 directly interacts with the monitor module 402, and a more detailed description of module 408 is provided below in connection with FIGS. 8 and 9.

The diagnostic index derivation module 410 generates the data values utilized in the diagnostic process. The task includes, but is not limited to, identifying frequency pairs of interest through the use of predetermined clinical reference arrays and creating a diagnostic index from the values in the bispectral data arrays at the frequency locations defined by the reference array. Module 410 directly interacts with the monitor module 402, and a more detailed description of module 410 is provided below in connection with FIG. 11.

Figure 5:
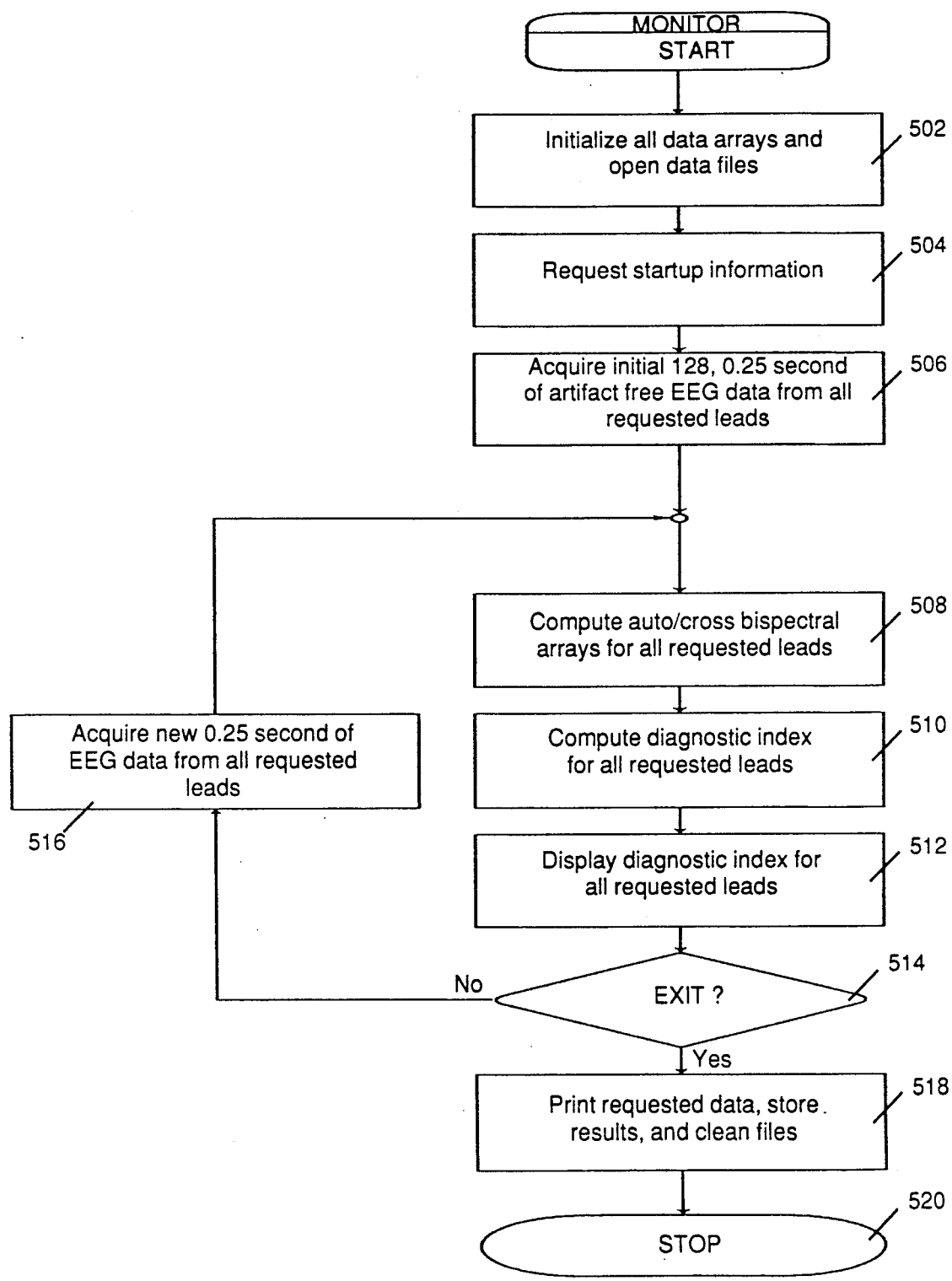
FIG. 5 is a flow chart of the operations of the monitor module shown in FIG. 4.

Referring now to FIG. 5, the operation of the monitor module 402 will now be discussed. In step 502, the data arrays used to store the digitized EEG, the 128 0.25 second EEG data records, and the bispectral data of each lead are initialized. The data files required for storage and files containing data bases required for the computation of diagnostic indices are also opened in the initializing step 502.

In step 504 the system requests the information required to start the acquisition and diagnostic process from the user via the user interface module 404. This requested information includes patient descriptive statistics (sex, age, clinical symptoms etc..), type of diagnostic procedure to be conducted, and the leads used for autobispectral analysis and the leads used for crossbispectral analysis.

The system includes a default mode of operation and in this default mode the system continuously monitors the depth and adequacy of anesthesia, and any pain responses during surgical stress utilizing a default autobispectral density database. Default band pass filtering is performed from 2 to 500 Hz; the default sampling rate is set at 2000 Hz; and default gain is automatically adjusted to achieve maximum dynamic range in each lead. The following discussion of the monitor module 402 will utilize the default settings of the system.

The EEG signals measured by leads Fp1, Fp2, F7, F3, Fz, F4, F8, T3, C3, Cz, C4, T4, T5, P3, Pz, P4, T6, 01, and 02 (A1 or A2 for reference) are used for autobispectral analysis.

The EEG signals measured from the difference of leads F7 and T3 (F7-T3) and the difference of leads F8 and T4 (F8-T4) originate from the area covered by the frontal left hemisphere and frontal right hemisphere regions respectively. These signals from F7-T3 and F8-T4 are paired and used for crossbispectral analysis. In this way, the interhemispheric relationships for the frontal region can be examined. Similarly, pairing C3-Cz with C4-Cz and T3-T5 with T4-T6 for crossbispectral analysis purposes allows for the examination of the interhemispheric relationships of the occipital and parietal regions respectively.

In step 506, 128 0.25 second buffers of artifact free raw EEG data ar acquired. All channels transmitting artifactual data are properly signaled to the operator to correct the problem.

The system, in step 508, computes autobispectral arrays for leads Fp1, Fp2, F7, F3, Fz, F4, F8, T3, C3, Cz, C4, T4, T5, P3, Pz, P4, T6, 01, 02, and crossbispectral arrays for leads F7-T3 paired with F8-T4, T3-T5 paired with T4-T6, and C3-Cz paired with C4-Cz. Other leads may, of course, be used in the computation of these arrays, and two different approaches for bispectral computation will be discussed below with reference to FIGS. 8 and 9.

In step 510, the single number diagnostic indices from all generated autobispectral and crossbispectral arrays are computed. Autobispectral density and crossbispectral density clinical reference arrays are utilized in these diagnostic index computations. The generation of the reference arrays is discussed later. The system instantaneously displays, in step 512, all computed diagnostic indices for all leads being analyzed. In step 514, the system checks for an exit request, and if such a request has not been made, the system, in step 516, acquires a new 0.25 second buffer and repeats steps 508 through 514. In step 518, requested printouts are produced, results are stored to disk for archival purposes and all files are closed. In step 520, the process is terminated.

Figure 6:
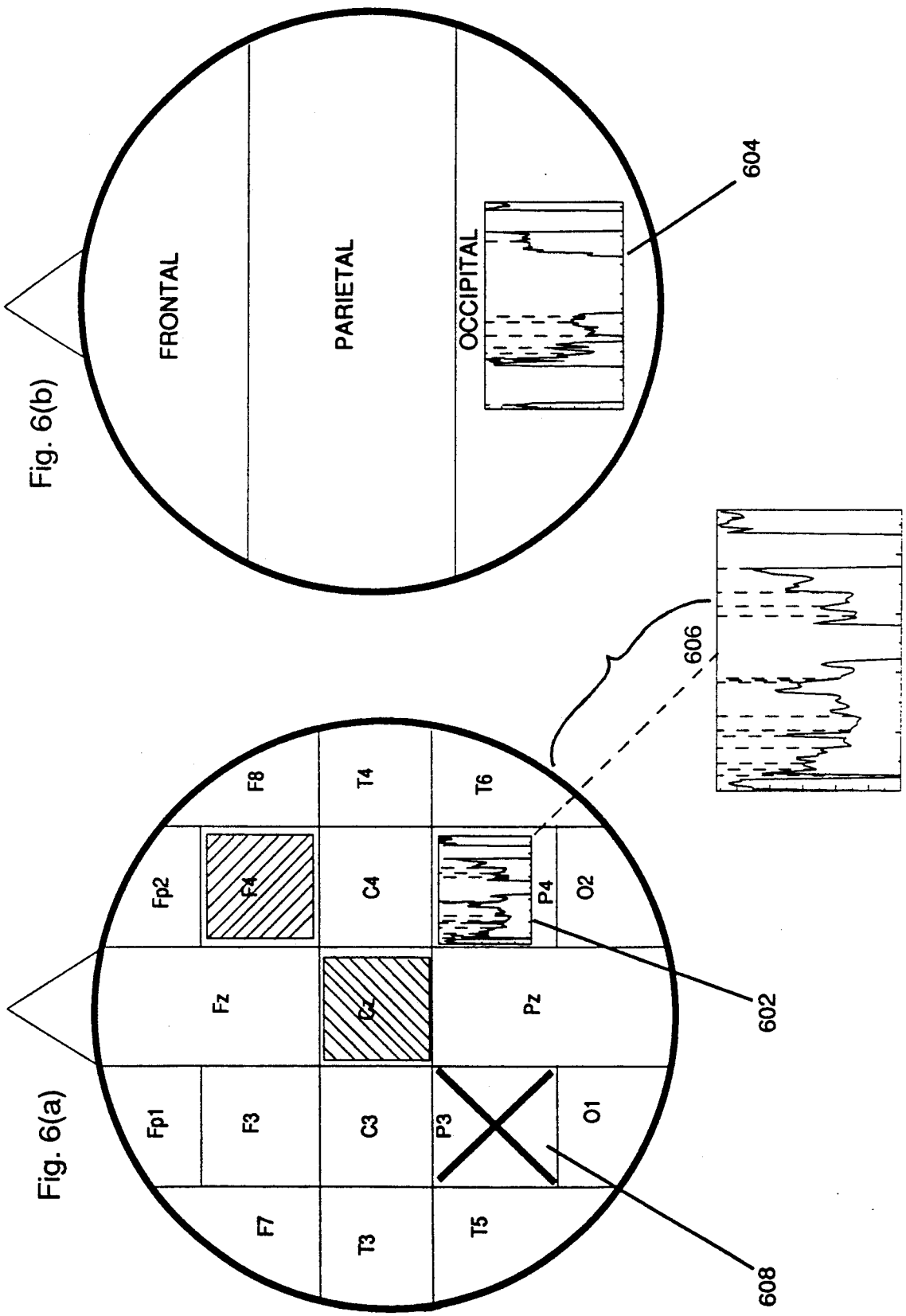
FIG. 6 is a view of a sample display representation of bispectral values generated by the system of FIG. 1.

A sample display representation generated by the system is shown in FIG. 6. Representations of the patient's head are shown on the graphics display in FIG. 6(a) and FIG. 6(b). The first illustration FIG. 6(a) is divided into nineteen sections each representing the region probed by an electrode. The second illustration FIG. 6(b) is divided into three horizontal sections representing combined left and right hemisphere activity probed by the group of electrodes in that region.

For head representation FIG. 6(a), each section contains a compressed continuous tracing 602 of the computed diagnostic index utilizing the unipolar EEG data acquired from the electrode in that site. For head representation FIG. 6(b), each section contains a compressed continuous tracing 604 of the computed crossbispectral diagnostic index utilizing bipolar EEG data acquired from several electrodes in that site.

At the request of the operator any site can be displayed as an enlarged view 606 for closer examination. The background of the tracing of each site (such as 602 or 604) is color coded to reflect the possible values allowed for in the rang of the selected diagnostic index. The most current value of the diagnostic index for that site will dictate what color is displayed in the background (e.g. Red =lowest value to Green =highest value). This will facilitate the examination of the patient's status at a distance. Each site will be covered by a large "X" 608 if a lead fail or a artifact was detected for any of the leads contributing to the data required to generate the diagnostic index at that site.

Figure 7:
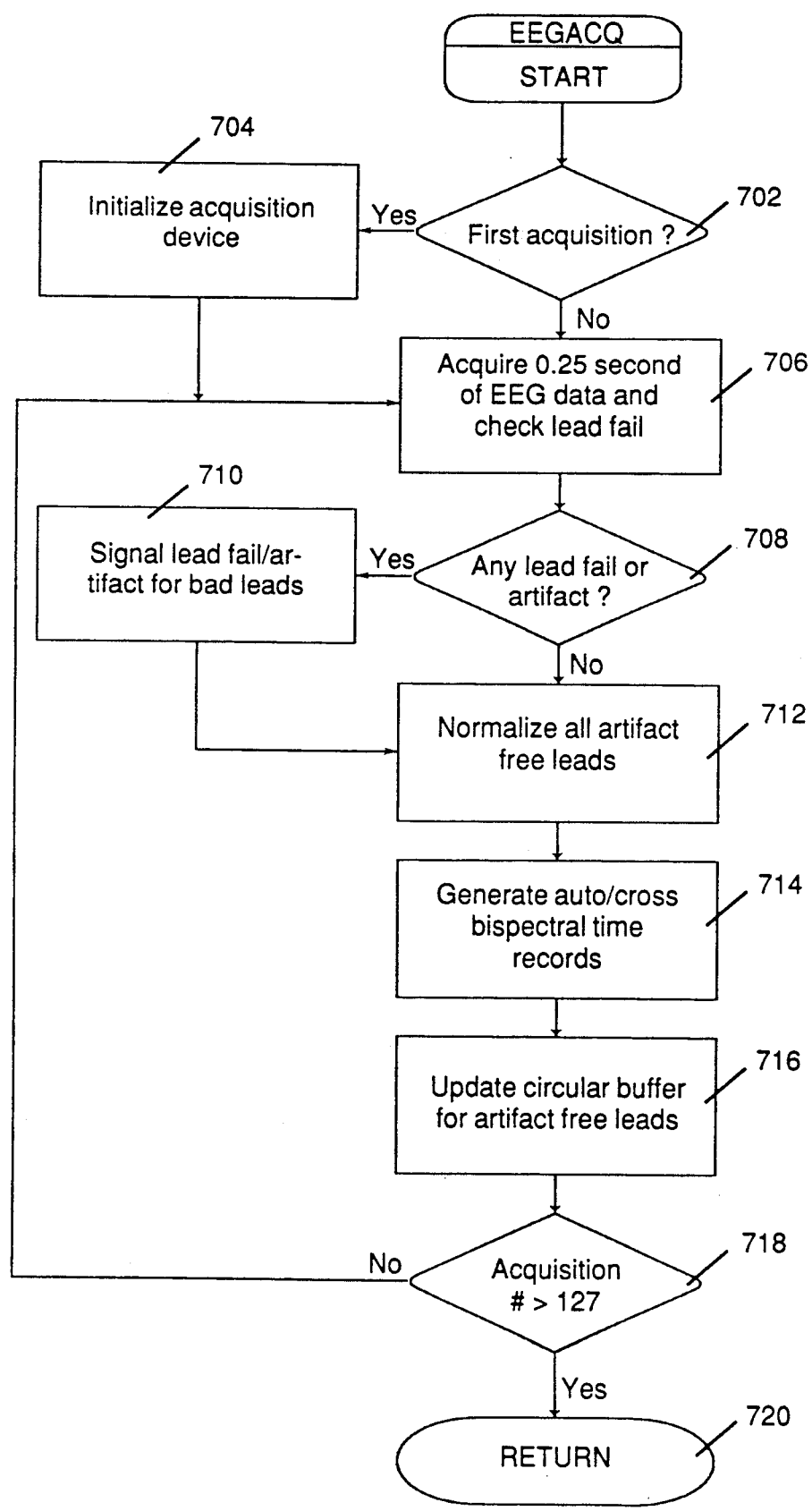
FIG. 7 is a flow chart of the operations of the acquisition and EEG raw data management module of the system shown in FIG. 4.

Referring to FIG. 7, the acquisition and raw EEG data management module 406 will now be described in greater detail. In step 702, the system checks whether the 0.25 second buffer for which data is to be acquired is the first buffer being filled for that run, and if it is, the acquisition system 12 in step 704 is supplied with requested filtering, gain, sampling rate and lead selection information. The default settings are band pass 2–500 Hz for filtering, 50,000 for gain, 2,000 samples/sec for sampling rate and signals from all 19 leads are acquired.

In step 706, the acquisition system 12 acquires data for each 0.25 second buffer for all requested leads and transfers this data to the host computer 18. The system detects lead fails during the acquisition cycle in step 708 by checking for very large positive or negative values. Also in step 708 a publicly available algorithm is used to check for artifact in each lead. In step 710, leads generating failed and artifactual data are marked for the monitor module 402.

In step 712, the system normalizes the records of data acquired from all artifact free leads by subtracting the mean of the samples in each record from each sample in that record, and then dividing the sample by the standard deviation of the records. This normalization sets the variance in each record to 1 and has the effect of weighing each record equally during bispectral averaging. The process is therefore less dependent on the absolute power spectral density at any frequency band.

In step 714, each 0.25 second record from each of the leads Fp1, Fp2, F7, F3, Fz, F4, F8, T3, C3, Cz, C4, T4, T5, P3, Pz, P4, T6, 01, 02 is assigned to an $X_i(t)$, where $X_i(t)$ are the individual time series records provided for autobispectral processing Also in step 714, the frontal left hemisphere time series, $X_i(t)$, from F7-T3 and the frontal right hemisphere time series, $Y_i(t)$, from F8-T4 are provided for crossbispectral processing. Similarly, by pairing leads C3-Cz with C4-Cz and T3-T5 with T4-T6, the cross bispectrum of the left and right occipital and left and right parietal regions respectively can be processed. It should be noted that for autobispectral analysis $Y_i(t)$ is set to equal $X_i(t)$ and in all cases the index i denotes the record number from 1 to 128.

In step 716, a circular buffer mechanism is used for storing the appropriate $X_i(t)$ and $Y_i(t)$ records for each lead. The buffer is updated by storing the most recently acquired data record in the location of the least recently acquired data record. In step 718, the program checks whether the circular buffer has 128 acquired data records to start bispectral analysis, and if there are 128 data records in the buffer, operation of the system returns to the monitor module 402 in step 720.

Referring now to FIG. 8, the frequency domain based procedures for producing the autobispectrum or the crossbispectrum will now be discussed. In step 802, the system checks whether the computation to be performed is an autobispectral or crossbispectral computation. Autobispectral analysis is a special case of crossbispectral analysis and therefore different rules of symmetry apply.

In step 804, the system sets the following symmetries in order to proceed with autobispectral computation:

$$f_1 + f_2 < N/2$$

where N=512 (0.25 secs * 2000 samples in a preferred embodiment), and $$0 < f_2 < f_1$$

$$X_i(t) = Y_i(t) \rightarrow X_i(f) = Y_i(f)$$

where $f_1$ and $f_2$ (also referred to as $F_1$ and $F_2$ or Frequency 1 and Frequency 2) denote the frequency pairs over which bispectral computation will be carried out. $X_i(t)$ and $Y_i(t)$ denote the individual time series records used for bispectral computation. $X_i(f)$ and $Y_i(f)$ denote the Fourier transform of the time series records and i denotes the record number and in this embodiment ranges from 1 to 128.

In step 806, the following symmetries are adhered to for crossbispectral analysis:

$$f_1 + f_2 < N/2$$

$$0 < f_1 < N/2$$

$$0 < f_2 < N/2$$

$$-2f_2 < f_1$$

$$X_i(t) \neq Y_i(t) \rightarrow X_i(f) \neq Y_i(f)$$

where all variables represent the same values as they do for autobispectral analysis, except that for crossbispectral analysis $X_i(t)$ and $Y_i(t)$ represent individually derived time series records from left and right hemisphere leads respectively.

The fast Fourier transform (FFT) $X_i(f)$ and $Y_i(f)$ of each record of the 128 selected records for that lead, is computed using a standard IEEE library routine or any other publicly available routine in step 808.

In Step 810, the power spectra $P_{xi}(f)$ and $P_{yi}(f)$ of each record of the 128 selected records for that lead is computed by squaring the magnitudes of each element of the Fourier transform $X_i(f)$ and $Y_i(f)$ respectively.

The system computes the average complex triple product in step 812 by utilizing the following equations where $bc_i(f_1,f_2)$ is an individual complex triple product from one record in a given lead and $BC(f_1,f_2)$ is the average complex triple product for that same lead:

$$bc_i(f_1,f_2) = X_i(f_1) * Y_i(f_2) * Y_i^*(f_1+f_2)$$

where $Y_i^*(f_1,f_2)$ is the complex conjugate of $Y_i(f_1+f_2)$, and $$BC(f_1,f_2) = \frac{1}{128} \sum_{i=1}^{128} bc_i(f_1,f_2)$$

The average real triple product is computed in step 814 by using the following equations where $br_i(f,f_2)$ is an individual real triple product from one record in a given lead and $BR(f_1,f_2)$ is the average real triple product for that same lead:

$$br_i(f_1,f_2) = P_{xi}(f_1) * P_{yi}(f_2) * P_{yi}(f_1 + f_2)$$

$$BR(f_1,f_2) = \frac{1}{128} \sum_{i=1}^{128} br_i(f_1,f_2)$$

In step 816, the array of auto/crossbispectral density values ($BD(f_1,f_2)$) is computed using the following equation:

$$BD(f_1,f_2) = |BC(f_1,f_2)|$$

In step 818, the system computes the array of auto/crossbiphase values ($\phi(f_1,f_2)$) using the following equation:

$$\phi(f_1,f_2) = \tan^{-1}[\text{Im}(BC(f_1,f_2))/\text{Re}(BC(f_1,f_2))]$$

$$0 < \phi < 2\pi \text{ (radians)}$$

In step 820, the system computes the array of auto/crossbicoherence values ($R(f,f_2)$) using the following equation:

$$R(f_1,f_2) = BD(f_1,f_2)/[BR(f_1,f_2)]^{\frac{1}{2}}$$

$$0 < R < 1$$

In step 822, the system returns the requested auto/cross bispectral density, bicoherence, biphase arrays to the monitor module 402.

Now turning to FIG. 9, a parametric based method for producing the autobispectrum and the crossbispectrum will now be described. In steps 902, 904, and 906 the system sets the symmetries and time series records in the same manner as described above in steps 802, 804, and 806 respectively. The power spectra of $X_i(t)$ and $Y_i(t)$ are estimated in steps 908, 910, and 912. This estimation method includes two major stages, the Autoregressive (AR) model order selection and the power spectrum computation for $X_i(t)$ and $Y_i(t)$. In step 908, the system computes two sequences of autocorrelations, $\{R_{2x}(m)\}$ and $\{R_{2y}(m)\}$ using the following equation.

$$R_{2z}(m) = \frac{1}{M*N} \sum_{i=1}^{M} \sum_{t=0}^{N-|m|} z_i(t)z_i(t+m),$$

$$z = X, Y, \text{ and } m = 0, 1, \ldots, L$$

where M is the number of records of each lead (128 in our case), and N is the number of samples per record (512 in our case), and L is much greater than the possible AR filter order (we choose 50). The Final Prediction Errors, $FPE_X(m)$ and $FPE_Y(m)$ are calculated for all orders, $m = 2, 2, \ldots L$, by performing a Levinson recursion function on each autocorrelation sequence in step 910 in order to find the order of the AR filter. The locations, $Q_X$ and $Q_Y$, of the minimum of $FPE_X(m)$ and $FPE_Y(m)$ respectively are chosen to be the orders of the AR filters of power spectra of $X_i(t)$ and $Y_i(t)$ respectively, i.e., $$FPE_X(Q_X) = \min\{FPE_X(m)\} \text{ and } FPE_Y(Q_Y) = \min\{FPE_Y(m)\}$$

Once the orders of the AR filters for power spectra are chosen, the autocorrelation sequences, $\{R_{2x}(m)\}$ and $\{R_{2y}(m)\}$, are entered into Levinson recursion with order $Q_X$ and $Q_Y$, respectively, instead of L. The coefficients, $\{c_{ix}, i=0, 1, \ldots, Q_X\}$ and $\{c_{iy}, i=0, 1, \ldots, Q_Y\}$, obtained from the recursion are the coefficients of the AR filters for power spectra of $X_i(t)$ and $Y_i(t)$ respectively. Then, in step 912, the power spectra $P_X(f)$ and $P_Y(f)$ are computed as the prediction error ($\sigma_z^2$) divided by square of the magnitude of the Fourier transform of the coefficients, i.e., $$P_z(f) = \frac{\sigma_z^2}{\left|1 + \sum_{i=1}^{Q_z} c_{iz} e^{-j2\pi fi}\right|^2}, z = X, Y.$$

The system estimates the auto/cross bispectrum in steps 914, 916, and 918. The estimation process includes two major stages: the order selection and bispectrum computation. In step 914, two sequences of third-order moments, $\{R_{3X}(\tau)\}$ and $\{R_{3Y}(\tau)\}$ are computed using the following equation.

$$R_{3z}(\tau) = \frac{1}{M*N} \sum_{i=1}^{M} \sum_{t=s_1}^{s_2} z_i(t)z_i^2(t+\tau),$$

$$z = X, Y, \text{ and } \tau = -L, \ldots, L$$

where $s_1 = \max(1, 1-\tau)$, $s_2 = \min(N, N-\tau)$, and L is much greater than the possible AR filter orders (e.g. 50).

In step 916, two super matrices $T_X$ and $T_Y$ are formed as follows.

$$T_z = \begin{pmatrix} R_{3z}(-L) & R_{3z}(-L+1) & \ldots & R_{3z}(0) \\ R_{3z}(-L-1) & R_{3z}(-L) & \ldots & R_{3z}(-1) \\ \cdot & \cdot & & \cdot \\ \cdot & \cdot & \ldots & \cdot \\ \cdot & \cdot & & \cdot \\ R_{3z}(-2L) & R_{3z}(-2L+1) & \ldots & R_{3z}(-L) \end{pmatrix}, z = X, Y.$$

From the assumption we made about the AR filter of bispectrum, the orders $O_X$ and $O_Y$ of the AR filters of bispectra of $X_i(t)$ and $Y_i(t)$ are the ranks of the super matrices $T_X$ and $T_Y$. Therefore, $O_X$ and $O_Y$ are chosen by using singular value decomposition. Having found the orders, we obtain the coefficients of the AR filters of bispectra by solving the following linear system of equations:

$$\begin{pmatrix} R_{3z}(0) & R_{3z}(1) & \ldots & R_{3z}(O_z) \\ R_{3z}(-1) & R_{3z}(0) & \ldots & R_{3z}(O_z-1) \\ \cdot & \cdot & & \cdot \\ \cdot & \cdot & \ldots & \cdot \\ \cdot & \cdot & & \cdot \\ R_{3z}(-O_z) & R_{3z}(-O_z+1) & \ldots & R_{3z}(0) \end{pmatrix} \begin{pmatrix} 1 \\ b_{1z} \\ \cdot \\ \cdot \\ \cdot \\ b_{O_z z} \end{pmatrix} =$$

$$\begin{pmatrix} \beta_z \\ 0 \\ \cdot \\ \cdot \\ \cdot \\ 0 \end{pmatrix}, z = X, Y.$$

where the skewness ($\beta_x$) and the coefficients ($b_{1z}, \ldots, b_{0zz}$), $z = X, Y$, can be obtained by solving the linear system of equations.

The auto/cross bispectrum of $X_i(t)$ and $Y_i(t)$ are computed in step 918 as the cubic root of the triple product of the skewnesses $(\beta_X \beta_Y \beta_Y)^{\frac{1}{3}}$ divided by the triple product of the Fourier transforms of the AR filter coefficients ($H_z(f)$), i.e., $$BC(f_1, f_2) = (\beta_X \beta_Y \beta_Y)^{\frac{1}{3}}/H_X(f_1)H_Y(f_2)H_Y^*(f_1 + f_2)$$

$$H_z(f) = 1 + \sum_{i=1}^{O_z} b_{iz} e^{-j2\pi f i}, z = X, Y.$$

and $BR(f_1, f_2)$ is the real triple product for that same lead:

$$BR(f_1, f_2) = P_X(f_1) * P_Y(f_2) * P_Y(f_1 + f_2)$$

After obtaining power spectrum and auto/cross bispectrum, the system computes the bispectral density array, the biphase, and the bicoherence in step 920 the same way as in steps 816, 818, 820. In step 922, the system returns to the monitor module 402 the requested bispectral density, biphase, and bicoherence arrays.

Figure 10A:
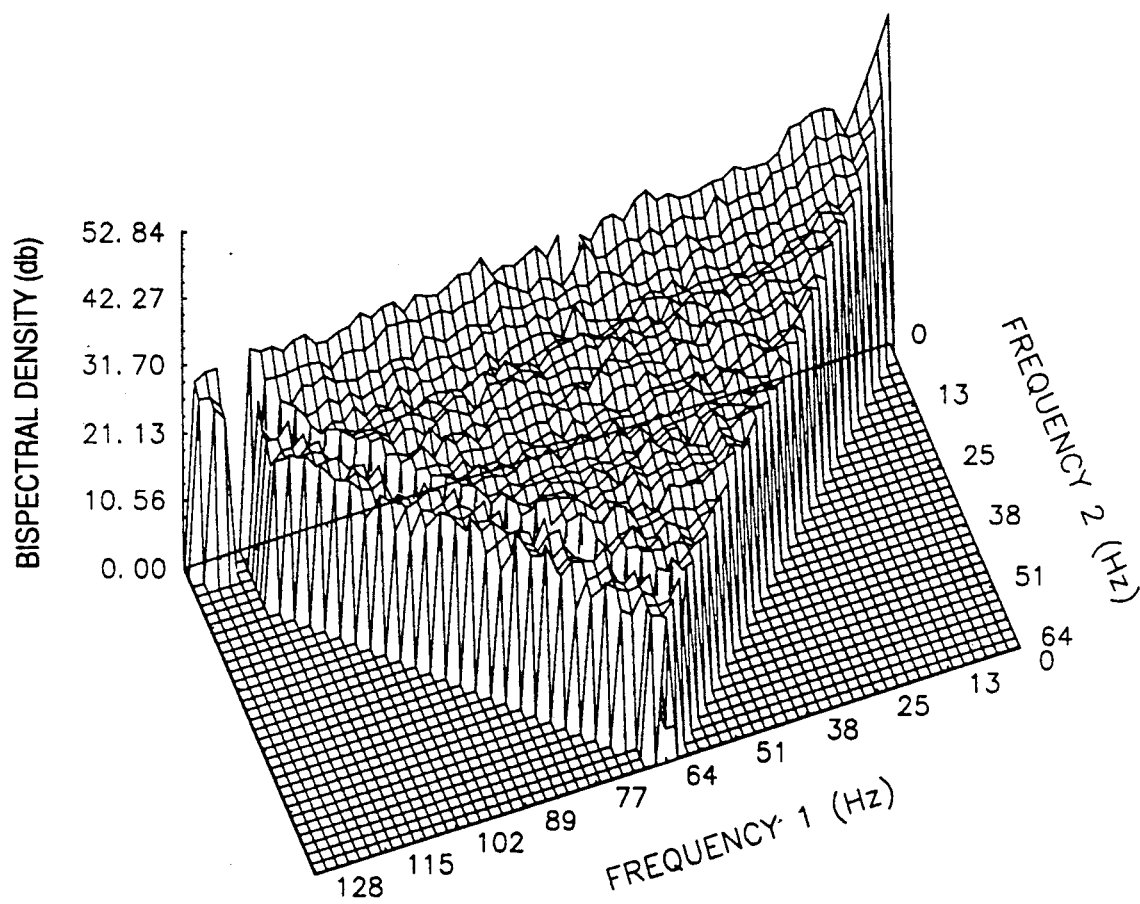
FIG. 10($a$) is an illustration of a graph showing a bispectral density array generated by the system of FIG. 1.
Figure 10B:
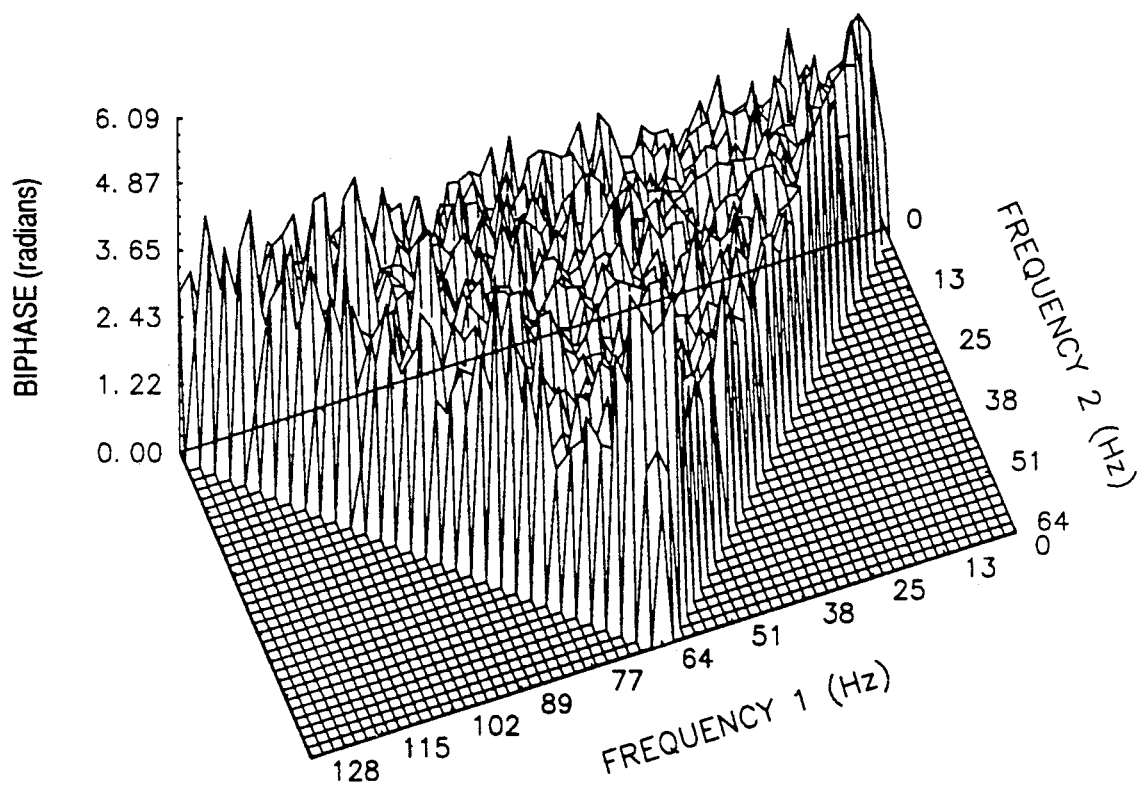
Figure 10C:
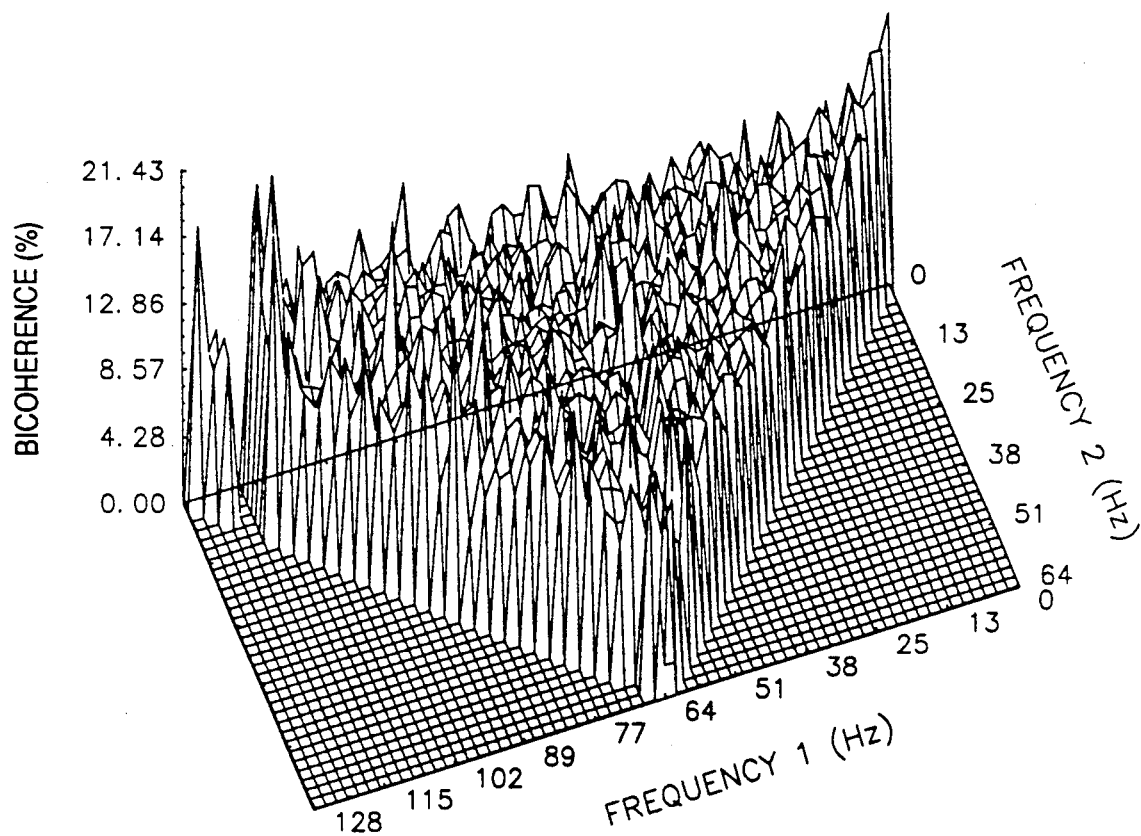

For illustration purposed FIG. 10 contains sample autobispectral arrays showing frequency pairs $0 < f_1 < 128$ Hz, and $0 < f_2 < 64$ Hz. A bispectral density array is shown in FIG. 10(a) where the Z axis represents the magnitude in decibels (db) of the coupled interaction between all appropriate frequency pairs $f_1$ and $f_2$. Recall that the frequency pairing scheme must adhere to the symmetry rule:

$$f_1 + f_2 < N/2$$

where $N = 256$ Hz in this case. A bicoherence array is shown in FIG. 10(c) where the Z axis represents the normalized magnitude in percent (%) of the coupled interaction between all appropriate frequency pairs $F_1$ and $f_2$. A biphase array is shown in FIG. 10(b) where the Z axis represents the phase in radians of the coupled interaction between all appropriate frequency pairs $f_1$ and $f_2$.

Figure 11:
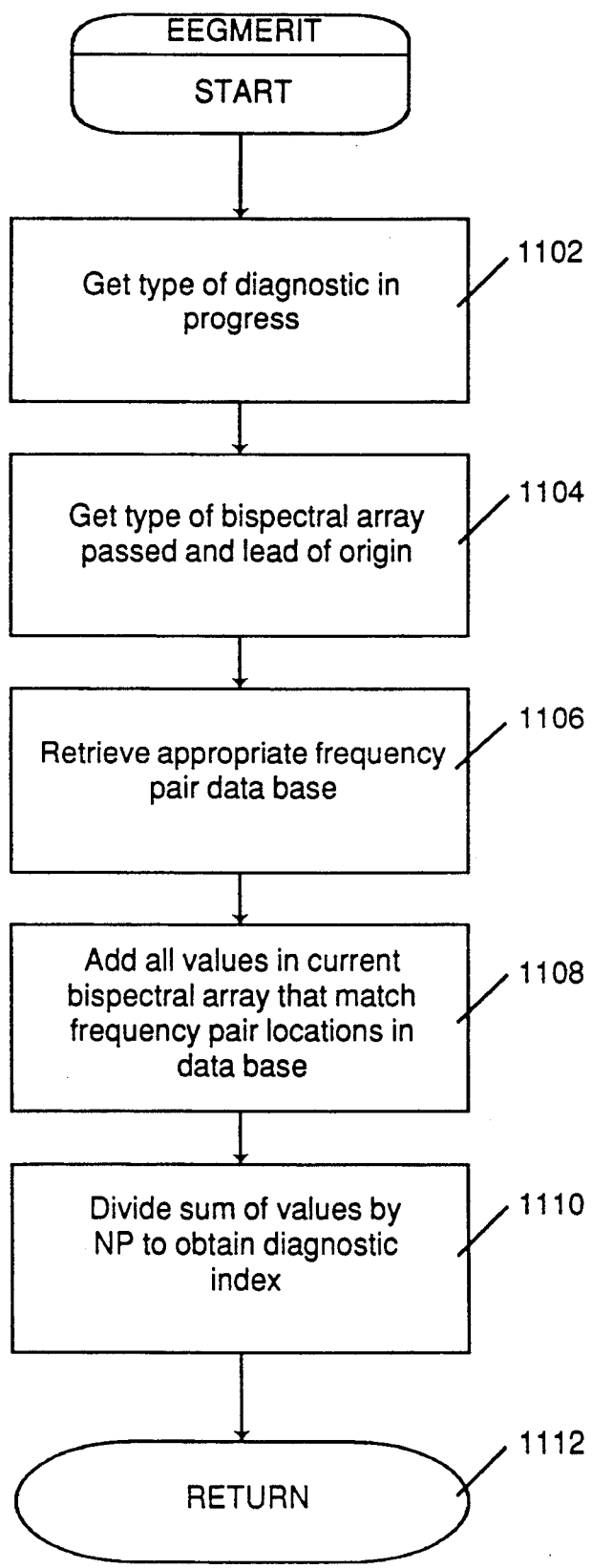
FIG. 11 is a flow chart of the diagnostic index generation module shown in FIG. 4.

Referring now to FIG. 11 a more detailed description of the diagnostic index generation module 410 will now be provided. In step 1102, the system identifies the type of diagnostic assessment in progress. In a preferred embodiment the four possible options are:
1. Depth of anesthesia/pain & surgical stress.
2. Cerebral ischemia.
3. Cerebral intoxication (alcohol, narcotics).
4. Cognitive process evaluation.

In step 1104, the system identifies the type of bispectral array to pass for use in the diagnostic index computation after a user selects a specific lead and array type as described above with respect to the user interface module 404. There are three (3) possible options for each unipolar lead: autobispectral density; autobiphase; autobicoherence. There are also three (3) possible options for each set of bipolar leads: crossbispectral density; crossbiphase; crossbicoherence. Since there are 57 (3×19 leads) different types of autobispectral and 9 (3×3 sets) types of crossbispectral arrays for each one of the 4 diagnostics, the total number of databases is 264.

In step 1106, the appropriate reference array is retrieved from resident memory (or from disk). Each reference array will contain the locations for the frequency pairs which are most sensitive to the assessment in progress (the generation of the reference arrays and the selection of defaults will be discussed later). In step 1108, the system adds all data points in the bispectral array at the locations identified by the retrieved reference array. A counter (NP) of the total number of points added is kept. In step 1110, the sum of the data points is divided by NP to obtain the single number diagnostic index. In step 1112, the program returns to the monitor module 402.

The predetermined clinical reference arrays referred to above are critical to the device's ability to achieve clinically relevant diagnostic efficacy. In the following section we discuss the process adopted for generating these clinical reference arrays. Since a total number of 276 possible reference arrays exist, only one will be discussed in detail. All other reference arrays are acquired in a similar fashion. For illustration purposes the generation of the autobispectral density reference array for monitoring depth of anesthesia with lead T3 will be reviewed.

In a first study EEG potentials from a small group of medically healthy surgical patients (N) with no known neurological disorders are recorded during routine surgery. The acquisition procedure described previously is followed, with the following exception:
Band pass filter 0.1–500 Hz For all patients, two minutes of artifact free EEG data are acquired under each of the following conditions:
Pre-operative; awake ("control")
Deep anesthesia; defined by conventional clinical standards (intervention or disease state)
Post-operative; alert in the recovery room (recovery from intervention, or after treatment of disease state)

An autobispectral density array is generated for lead T3 from each one of the three recordings for all patients, yielding a total of 3N arrays. The arrays are grouped in 3 sets of N arrays. The first representing the control state, the second representing intervention, and the third representing recovery.

A paired Student's t test is performed on each of 16,512 data points, comparing the first and second array. The resulting 16,512 t values are stored in a two dimensional array identical in structure to that of the bispectral density array. A second paired Student's t test is carried out on each of the 16,512 data points, comparing the second and third arrays. The resulting 16,512 t values are stored in a second two dimensional array identical in structure to that of the bispectral density array.

All t values not meeting a specific significance test or a specific confidence interval in either array are set to 0. In the preferred embodiment all locations with a t value not corresponding to a $p < 0.0001$ are set to 0. Each t value from the first t array ($T1(f_1, f_2)$) is compared with its corresponding t ($T2(f_1, f_2)$) from the second t array. One of the following conditions must be met:

$$T1(f_1,f_2) < 0 < T2(f_1,f_2)$$

or $T2(f_1,f_2) < 0 < T1(f_1,f_2)$

If neither one the two conditions is met at a particular frequency pair $f_1,f_2$ then $T1(f_1,f_2)=0$ and $T2(f_1,f_2)=0$.

The application of the above conditions has the effect of identifying all of the frequency pair locations that change significantly by showing a consistent increase in bispectral density value with anesthesia followed by a decrease with recovery, or a decrease with anesthesia followed by an increase with recovery.

Finally, the absolute values of the t values in each $f_1f_2$ locations from the first t array are added to their counterpart in the second t array to form a third t array. The third t array is an average of the first two and can be visually inspected for highly sensitive regions.

The last step involves sorting the third t array for the most sensitive ensemble of frequency pair locations. In the preferred embodiment this would consist of the top 25% of all t values. The locations $f_1$, $f_2$ of the most significant t values meeting all of the above conditions are stored in resident memory (or on disk) as one of the predetermined reference arrays. This reference array will be accessed by the diagnostic index derivation module 410, for autobispectral density diagnostic index generation during anesthesia/surgery for the location probed by lead T3.

For any particular diagnostic task and any particular lead there are 6 possible bispectral arrays (autobicoherence, autobispectral density, autobiphase, crossbicoherence, cross bispectral density, and crossbiphase) which could be examined for diagnostic potency. To rank order the reference arrays with respect to diagnostic efficacy a second prospective study is conducted. The conditions under which the study is conducted are identical to those of the first except that: (a) the frequency pair locations of interest have already been identified and are now followed prospectively and (b) the size of the study group is now sufficiently large so that sample variation of bispectral arrays more closely approximates the true variance within the population undergoing the intervention or suffering from the disease.

Thus for the example of anesthesia monitoring the EEG recording starts during the awake/control state and continues uninterrupted through the end of recovery. Continuous surgical notes are maintained throughout the operation After the completion of the study, continuous diagnostic indices are generated for the leads of interest for each of auto or cross bispectral density, biphase and bicoherence arrays. The continuous trends are annotated with the intraoperative notes. A sufficiently large group of prospective patients (determined b a statistical power test) is used to determine which continuous diagnostic index exhibits the greatest diagnostic efficacy on clinical grounds. The particular bispectral array used to generate this best diagnostic index during particular diagnostic procedure is programmed into the system as the default array for diagnostic assessment.

The following non-limiting example is provided solely for illustrative purposes. Twenty (20) patients undergoing elective surgery for a variety of orthopedic and gynecologic conditions were studied. Standard EEG leads were placed in 16 locations according to the International 10/20 system. Raw EEG signals were acquired, band-pass filtered (0.1-110 Hz) and digitized at a sampling rate of 256 Hz. EEG recordings were obtained from all patients prior to the induction of anesthesia. Patients were then anesthetized using standard techniques with a variety of anesthetic agents. Continuous EEG recordings were obtained during the period of anesthesia induction until the patient was judged to be adequately anesthetized for surgery by clinical assessment. Intermittent EEG recordings were when obtained during the course of the operation. During the period of recovery from anesthesia another continuous EEG recording was taken. A final recording was obtained when the patient was deemed to be "awake" in the recovery room. Detailed clinical intra-operative notes of patient status were maintained during all phases of EEG recording for subsequent correlation with bispectral parameters.

Figure 12A:
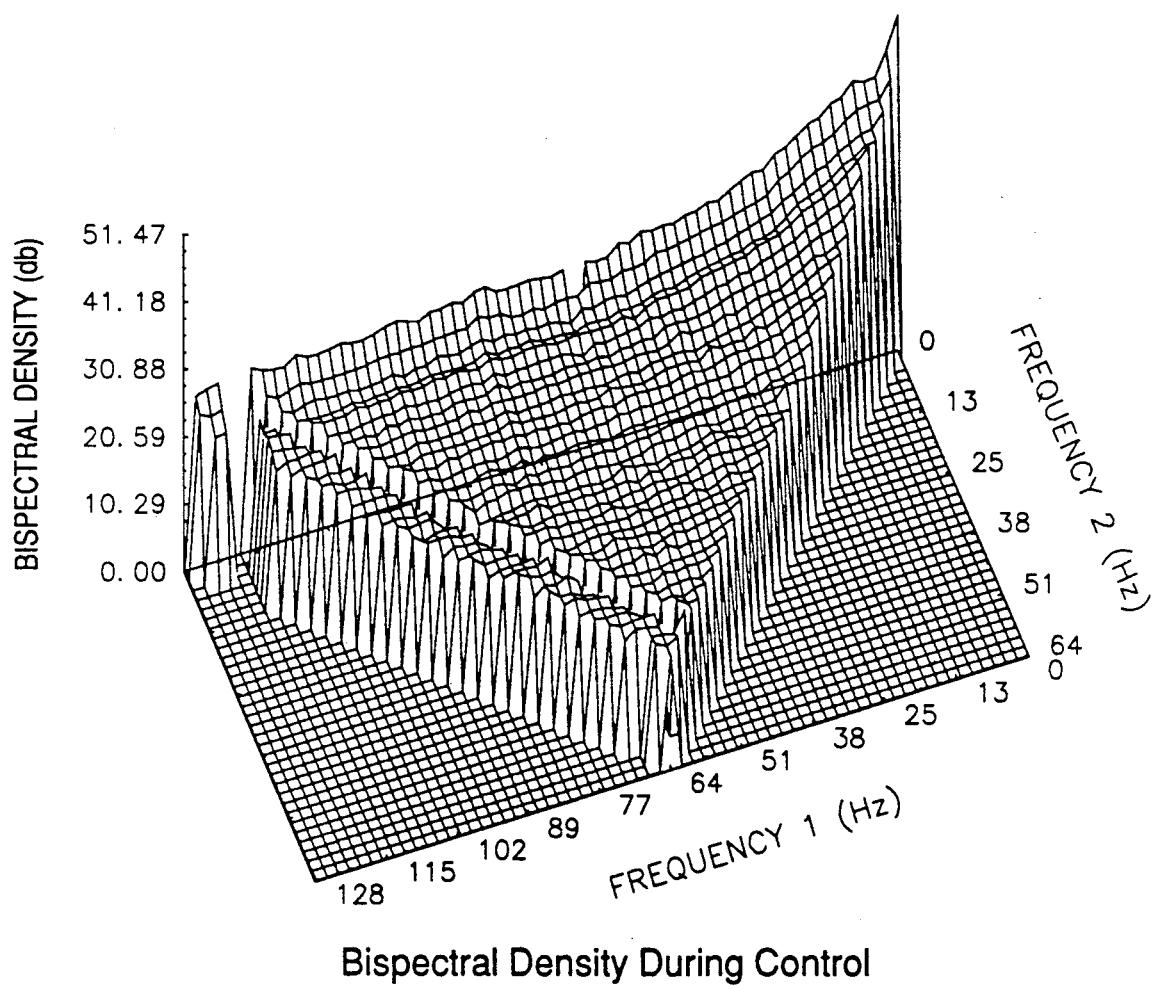
FIGS. 12($a$)–12($c$) are illustrations of arrays of bispectral density values for three different states of one patient.
Figure 12B:
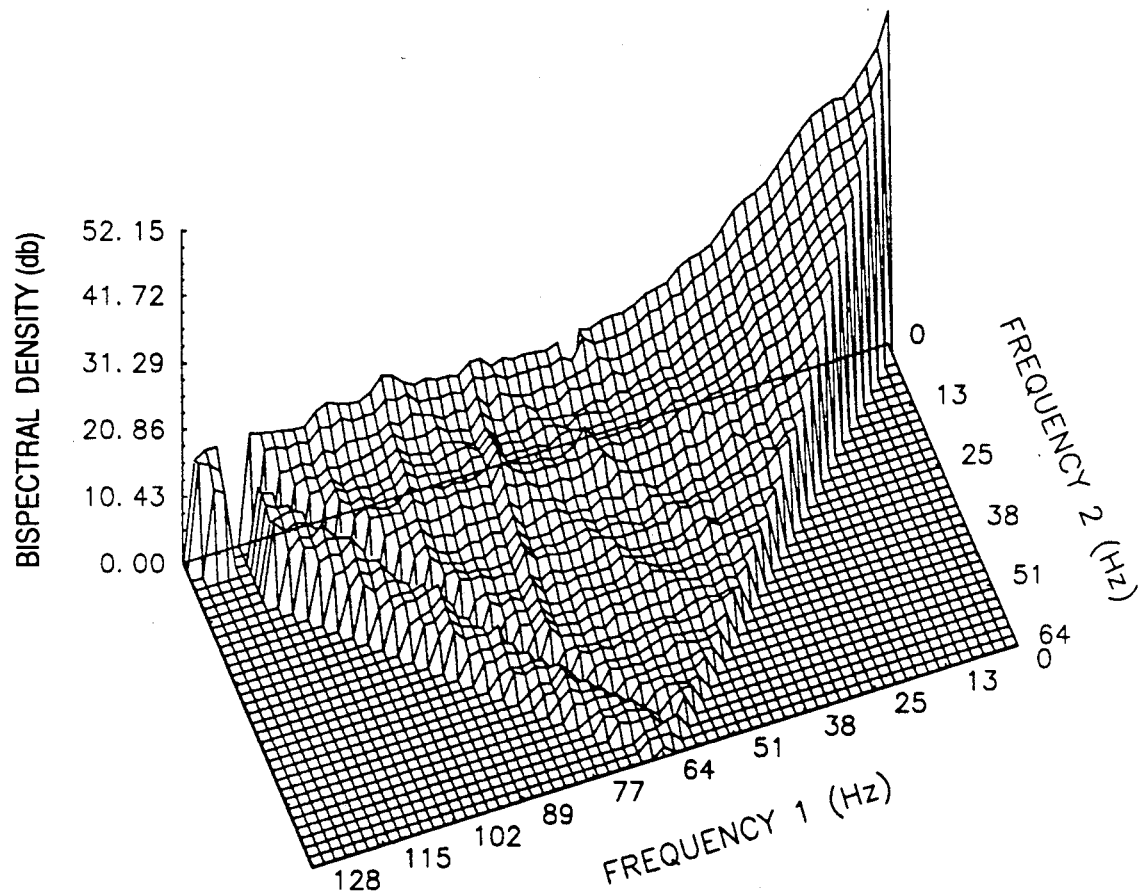
Figure 12C:
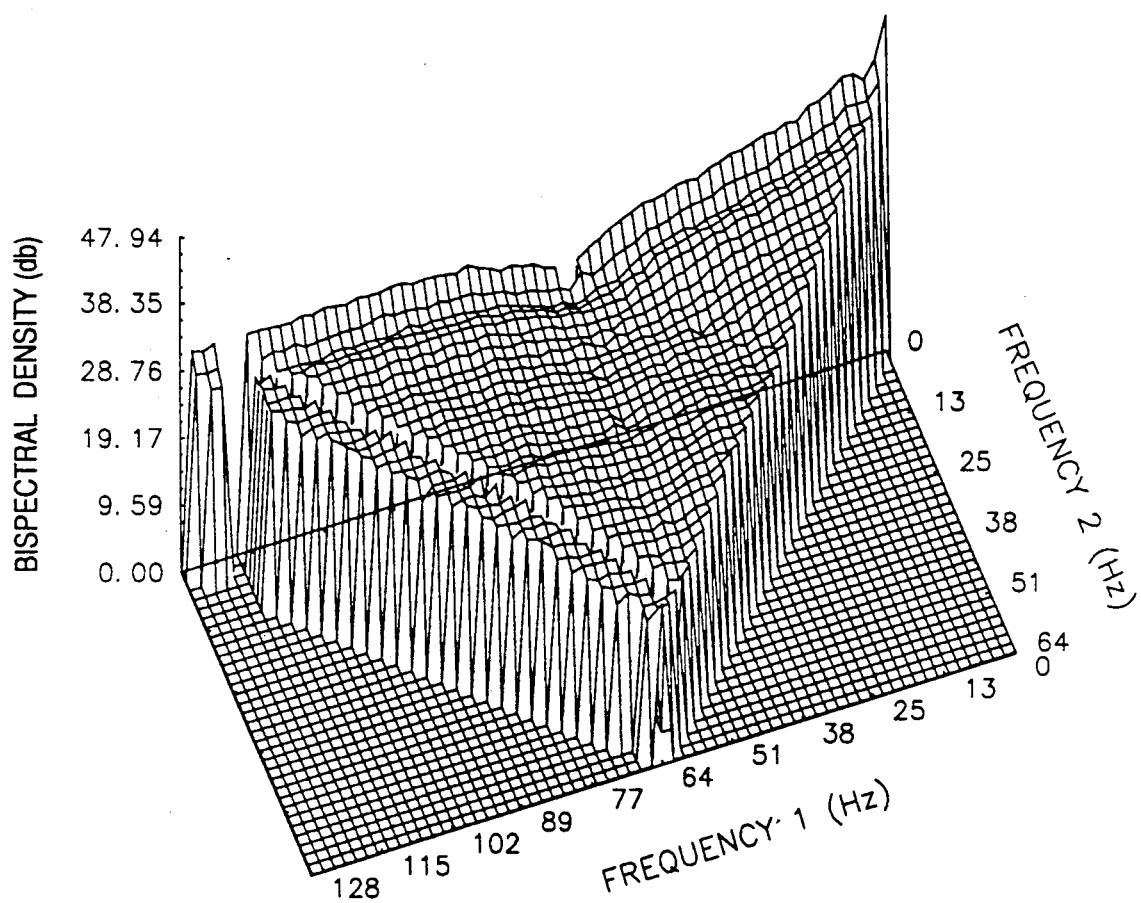

In 10 patients the entire available frequency spectrum (0.1 to 110 HZ) was examined for statistically significant changes in autobispectral density values from the awake state to the deeply anesthetized state and back to the awake state. FIGS. 12(a)–12(c) show average bispectral density arrays (from 10 patients) for each of the three states of consciousness. The method for determining statistical significance was as outlined above. FIGS. 13(a)–13(b) show the statistical arrays generated by the technique of the present invention the average t array for these 10 subjects for lead T3 for locations corresponding to a $p<0.05(t>2.26)$ (FIG. 13(a)) and the average t array for locations corresponding to a $p<0.0000003$ (t>10.0) (FIG. 13(b)). Each t value in the array reflects the consistency of change in a bispectral density value through the three states for one frequency pair location across all 10 patients. It is worth noting that virtually no data points are significant with a $p<0.0000003$ (t>10.0) in the frequency pair band of F1 below about 24 Hz and F2 below about 2 Hz in FIG. 13(b). On the other hand 7,168 locations were found to change with a $p<0.0000003$ (t>10.0) in the frequency pair band of F1 above about 24 Hz and F2 above about 2 Hz. The top 25% (7,168/4=1792 points) most significant high frequency locations were used to define the reference array. The autobispectral density index was calculated for each subject from the points defined by the reference array a described above in the detailed description of the invention. This autobispectral density index was then calculated as a continuous function for the continuous EEG recordings to assess its behavior during induction, intra-operatively, and during recovery. The correlation with clinical events during the operation was noted.

Figure 14:
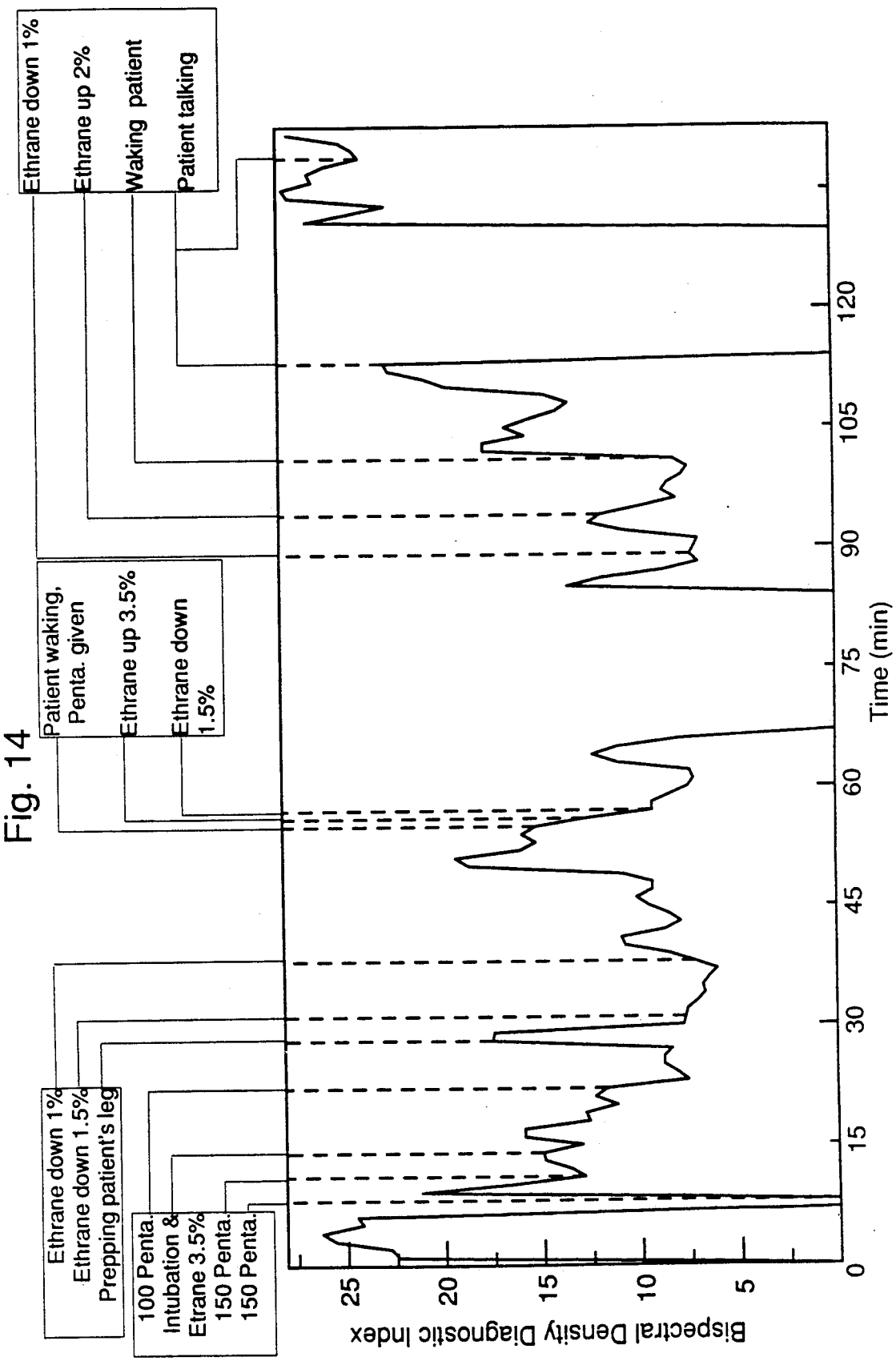
FIG. 14 is an annotated continuous autobispectral density diagnostic index graph for one lead generated by the system of FIG. 1.

A sample annotated continuous autobispectral density diagnostic index for lead T3 during surgery in a prospective subject is shown in FIG. 14. The index varies between 30 and 5 decibels and is quite sensitive to the patient's state of consciousness and the onset of painful stimuli. Specifically, the index drops with the induction of anesthetic agents (pentothal and ethrane) to the patient, and the index level rises as the patient's leg is being prepped for surgery. In addition, the index approaches its highest value when the patient is awake in the recovery room and most likely experiencing postoperative stress. (The gaps seen in the index plot correspond to time periods when EEG recordings were not being taken).

Similarly the above analytic process is used to generate the reference databases for cerebral ischemia, degrees of intoxication and normal or abnormal cerebral processes. In quantitatively detecting any of these cerebral phenomina, the system compares a number of autobispectral and crossbispectral EEG data from subjects in the normal state to clinically identified extremes of a certain physiologic state (awake vs anesthetized, sober vs intoxicated, perfused vs ischemic, at rest mentally vs thinking, normal vs retarded, etc..). The comparison utilizes a statistical approach to identify the bispectral data points that are most sensitive to the particular physiologic state in question. The frequency pair locations of the most sensitive data points are identified and stored in a database for reference purposes. When a diagnosis is to be carried out, the average of all the data points defined by the reference array is obtained for the subject undergoing the study. This average is used as a diagnostic index and is compared to a list of indices characteristic of each state by the operator or the system.

In addition to quantifying the depth and adequacy of anesthesia, pain responses during surgical stress, acute and chronic cerebral ischemia, level of consciousness, degree of cerebral intoxication and normal or abnormal cognitive processes, the system and method of the present invention may also be used to assess a myriad of cerebral phenomena based on the acquisition and processing of EEG signals into various bispectral arrays which are then compared to appropriate reference arrays.

Although bispectral analytic techniques in the frequency domain have been applied to the EEG signal, as was discussed in the Background above, parametric approaches to the estimation of bispectral values have not. Furthermore no bispectral technique has ever been demonstrated to be useful for any diagnostic purpose. Other techniques for the quantification of the depth of anesthesia or the detection and quantification of cerebral ischemia intraoperatively remain qualitative and limited in their overall utility and acceptance in practice. Specifically, the system and method of the present invention examines various bispectral values across all frequency pairs in a frequency range hitherto ignored by those knowledgeable in the art and uses the summed degree of changes in autobicoherence/autobispectral density/autobiphase, crossbicoherence/crossbispectral density/crossbiphase at a limited number of frequency locations as a index of physiological perturbation. The system and method utilize various bispectral arrays of defined clinical populations to define the locations of the subset of frequencies used t calculate this index. Reference clinical arrays are further utilized to assess the meaning of this index and to measure the significance of deviations of this index from normality. This allows the quantitative gauging of the disturbances in cerebral function, whether due to anesthesia, intoxicants or ischemia for any particular EEG lead position. The system and method disclosed herein also define the graphic display of the diagnostic index, whether on graphics screen or on paper, whether in real-time or in digital archive.

While the foregoing invention has been described with reference to its preferred embodiments, various alterations and modifications will occur to those skilled in the art. All such alterations and modifications are intended to fall within the scope of the appended claims.

What is claimed is:

1. A method of noninvasively detecting cerebral phenomena comprising the steps of:

acquiring electroencephalographic signals through at least one electrode from a body surface of a subject being analyzed;

filtering said electroencephalographic signals to obtain filtered signals having frequencies between 2 and 500 hertz;

dividing said filtered signals into a plurality of equally sized data records;

characterizing dynamic phase relations within said filtered signals by processing said filtered signals to generate bispectral values;

comparing said generated bispectral values to reference values to derive a diagnostic index that quantifies the detected cerebral phenomena.

2. The method of noninvasively detecting cerebral phenomena of claim 1 wherein the step of acquiring electroencephalographic signals further comprises the step of attaching electrodes to a head of the subject being analyzed in order to obtain a unipolar electroencephalographic signal from each region of interest of both left and right hemispheres of the subject's brain to which said electrodes are attached.

3. The method of noninvasively detecting cerebral phenomena of claim 1 wherein said bispectral values generated in said step of characterizing said dynamic phase relations are autobispectral density values.

4. The method of noninvasively detecting cerebral phenomena of claim 3 where said step of generating autobispectral density values comprises the steps of:

computing fast Fourier transforms $X_i(f)$ and $P_{Yi}(f)$ of each of said data records i;

computing power spectra $P_{Xi}(f)$ and $P_{Yi}(f)$ of said data records i by squaring the magnitude of each element of said fast Fourier transforms $X_i(f)$ and $Y_i(f)$ respectively;

computing for at least one electrode an average complex triple product of data records acquired by said at least one electrode;

computing for said at least one electrode an average real triple product of data records acquired by said at least one electrode;

computing for said at least one electrode an autobispectral density value as the absolute value of said average complex triple product for said electrode.

5. The method of noninvasively detecting cerebral phenomena of claim 4 further comprising the step of computing an autobiphase value $\phi(f_1,f_2)$ for at least one electrode such that:

$$\phi(f_1,f_2) = \tan^{-1}[Im(BC(f_1,f_2))/Re(BC(f_1,f_2))]$$

where $BC(f_1,f_2)$ is the average complex triple product for an electrode, and $f_1$ and $f_2$ designate limits of the frequency range over which the autobiphase computation is carried out.

6. The method of noninvasively detecting cerebral phenomena of claim 4 further comprising the step of computing an autobicoherence value $R(f_1,f_2)$ for at least one electrode such that $$R(f_1,f_2) = BD(f_1,f_2)/[BR(f_1,f_2)]^{1/2}$$

where $BD(f_1,f_2)$ is the autobispectral density value for said electrode, $BR(f_1,f_2)$ is the average real triple product for the same electrode, and $f_1$ and $f_2$ designate limits of the frequency range over which the autobicoherence computation is carried out.

7. The method of noninvasively detecting cerebral phenomena of claim 3 wherein said step of generating autobispectral density values comprises the steps of:
computing autocorrelation sequences $R_{2X}(m)$ and $R_{2Y}(m)$ of all data records acquired by at least one electrode;
determining the orders and coefficients of parametric models for power spectra of data records acquired by said at least one electrode;
computing power spectra $P_X(f)$ and $P_Y(f)$ of data records acquired by said at least one electrode;
computing third order moment sequences $R_{3X}(\tau)$ and $R_{3Y}(\tau)$ of data records acquired by said at least one electrode;
determining the orders and coefficients of parametric models of the bispectra of data records acquired by said at least one electrode;
computing for said at least one electrode a bispectrum of data records acquired by said at least one electrode.

8. The method of noninvasively detecting cerebral phenomena of claim 7 wherein said bispectrum is autobispectrum and further comprising the step of computing an autobispectral density value for at least one electrode as the absolute value of the bispectrum of all data records for said electrode.

9. The method of noninvasively detecting cerebral phenomena of claim 8 further comprising the steps of:
computing for at least one electrode a real triple product of data records acquired by said at least one electrode;
computing an autobicoherence value $R(f_1,f_2)$ for said at least one electrode such that $$R(f_1,f_2)=BD(f_1,f_2)/[BR(f_1,f_2)]^{1/2}$$

where $BD(f_1,f_2)$ is the autobispectral density value for an electrode, $BR(f_1,f_2)$ is the real triple product for the same electrode, and $f_1$ and $f_2$ designate limits of the frequency range over which bispectral computation is carried out.

10. The method of noninvasively detecting cerebral phenomena of claim 7 further comprising the step of computing an autobiphase value $\phi(f_1,f_2)$ for said at least one electrode such that:

$$\phi(f_1,f_2)=\tan^{-1}[Im(BC(f_1,f_2))/Re(BC(f_1,f_2))]$$

where $BC(f_1,f_2)$ is the bispectrum for an electrode, and $f_1$ and $f_2$ designate limits of the frequency range over which the bispectral computation is carried out.

11. The method of noninvasively detecting cerebral phenomena of claim 7 wherein said bispectrum is crossbispectrum and further comprising the step of computing a crossbispectral density value for each electrode pair as the absolute value of the crossbispectrum of all data records for each said electrode pair.

12. The method of noninvasively detecting cerebral phenomena of claim 11 further comprising the step of computing a crossbiphase value $\phi(f_1,f_2)$ for each of said at least one electrode pair such that:

$$\phi(f_1,f_2)=\tan^{-1}[Im(BC(f_1,f_2))/Re(BC(f_1,f_2))]$$

where $BC(f_1,f_2)$ is the crossbispectrum for an pair, and $f_1$ and $f_2$ designate limits of the frequency range over which the bispectral computation is carried out.

13. The method of noninvasively detecting cerebral phenomena of claim 12 further comprising the step of computing a crossbicoherence value $R(f_1,f_2)$ for each of said at least one electrode pair such that $$R(f_1,f_2)=BD(f_1,f_2)/[BR(f_1,f_2)]^{1/2}$$

where $BD(f_1,f_2)$ is the crossbispectral density value for an electrode pair, $BR(f_1,f_2)$ is the real triple product for the same electrode pair, and $f_1$ and $f_2$ designate limits of the frequency range over which bispectral computation is carried out.

14. The method of noninvasively detecting cerebral phenomena of claim 1 wherein said bispectral values generated in said step of characterizing said dynamic phase relations are autobicoherence values.

15. The method of noninvasively detecting cerebral phenomena of claim 1 wherein said bispectral values generated in said step of characterizing said dynamic phase relations are autobiphase values.

16. The method of noninvasively detecting cerebral phenomena of claim 1 wherein said step of acquiring electroencephalographic signals further comprises the step of attaching electrodes to the head of the subject being analyzed in order to obtain bipolar data sets of electroencephalographic signals from left and right hemispheres of the subject's brain to which said electrodes are attached.

17. The method of noninvasively detecting cerebral phenomena of claim 16 wherein one bipolar data set is acquired from a frontal left hemisphere of the subject's brain and another bipolar data set is acquired from a frontal right hemisphere of the subject's brain.

18. The method of noninvasively detecting cerebral phenomena of claim 16 wherein one bipolar data set is acquired from a left occipital region of the subject's brain and another bipolar data set is acquired from a right occipital region of the subject's brain.

19. The method of noninvasively detecting cerebral phenomena of claim 16 wherein one bipolar data set is acquired from a left parietal region of the subject's brain and another bipolar data set is acquired from a right parietal region of the subject's brain.

20. The method of noninvasively detecting cerebral phenomena of claim 1 wherein said bispectral values generated in said step of characterizing said dynamic phase relations are crossbispectral density values.

21. The method of noninvasively detecting cerebral phenomena of claim 20 where said step of generating said crossbispectral density values comprises the steps of:
computing fast Fourier transforms $X_i(f)$ and $Y_i(f)$ of said data records i;
computing power spectra $P_{Xi}(f)$ and $P_{Yi}(f)$ of said data records by squaring the magnitude of elements of said fast Fourier transforms $X_i(f)$ and $Y_i(f)$ respectively;
computing for at least one electrode pair an average complex triple product of all data records acquired by said at least one electrode pair;
computing for said at least one electrode pair an average real triple product of all data records acquired by each of said at least one electrode pair;
computing for said at least one electrode pair a crossbispectral density value as the absolute value of the average complex triple product for said electrode pair.

22. The method of noninvasively detecting cerebral phenomena of claim 21 further comprising the step of computing a crossbiphase value $\phi(f_1,f_2)$ for said at least one electrode pair such that:

$$\phi(f_1,f_2)=\tan^{-1}[\text{Im}(BC(f_1,f_2))/\text{Re}(BC(f_1,f_2))]$$

where $BC(f_1,f_2)$ is the average complex triple product for an electrode pair, and $f_1$ and $f_2$ designate limits of the frequency range over which the crossbiphase computation is carried out.

23. The method of noninvasively detecting cerebral phenomena of claim 22 further comprising the step of computing a crossbicoherence value $R(f_1,f_2)$ for said at least one electrode pair such that $$R(f_1,f_2)=BD(f_1,f_2)/[BR(f_1,f_2)]^{\frac{1}{2}}$$

where $BD(f_1,f_2)$ is the crossbispectral density value for an electrode pair, $BR(f_1,f_2)$ is the average real triple product for the same electrode pair, and $f_1$ and $f_2$ designate limits of the frequency range over which crossbicoherence computation is carried out.

24. The method of noninvasively detecting cerebral phenomena of claim 1 wherein said bispectral values generated in said step of characterizing said dynamic phase relations ar crossbicoherence values.

25. The method of noninvasively detecting cerebral phenomena of claim 1 wherein said bispectral values are generated in said step of characterizing said dynamic phase relations are crossbiphase values.

26. The method for noninvasively detecting cerebral phenomena of claim 1 wherein said step of acquiring electroencephalographic signals further comprises the step of analyzing said signals to determine lead failure.

27. The method of noninvasively detecting cerebral phenomena of claim 1 wherein said step of comparing further comprises the steps of:
 organizing said generated bispectral values in at least one array of bispectral values;
 selecting a physical phenomena to be diagnosed;
 retrieving an appropriate bispectral reference array from a resident memory, said reference array containing frequency pairs that are most sensitive to the physical phenomena to be diagnosed;
 adding data values in locations of each of said at least one array of bispectral values that are identified by the retrieved reference array as being locations containing data of significance to obtain a sum of said significant locations;
 averaging the values stored in said significant locations to generate a diagnostic index relating to the cerebral phenomena to be detected.

28. The method of noninvasively detecting cerebral phenomena of claim 1 further comprising the steps of:
 generating three arrays of bispectral data for each of three different states of the subject;
 performing a paired Student's t test comparing data in a first and a second array of said three arrays of bispectral data to produce a first t array and performing a paired Student's t test comparing data in said second and a third array of said three arrays of bispectral data to produce a second t array;
 comparing data values in said first t array with data values in corresponding locations in said second t array;
 identifying those corresponding locations in said first and second t arrays that differ by more than a preselected amount, said identified locations representing those locations that are significant for detecting the cerebral phenomena.

29. The method of noninvasively detecting cerebral phenomena of claim 1 wherein the cerebral phenomenon being detected is the depth of anesthesia in the subject being analyzed.

30. The method of noninvasively detecting cerebral phenomena of claim 1 wherein the cerebral phenomena being detected are pain responses during surgical stress in the subject being analyzed.

31. The method of noninvasively detecting cerebral phenomena of claim 1 wherein the cerebral phenomenon being detected is acute ischemia or infarction in the subject being analyzed.

32. The method of noninvasively detecting cerebral phenomena of claim 1 wherein the cerebral phenomenon being detected is the level of consciousness of the subject being analyzed.

33. The method of noninvasively detecting cerebral phenomena of claim 1 wherein the physical phenomenon being detected is the degree of cerebral intoxication of the subject being analyzed.

34. The method of noninvasively detecting physical phenomena of claim 1 wherein the physical phenomena being detected are normal or abnormal cognitive processes.

35. The method of noninvasively detecting cerebral phenomena of claim 1 further comprising the steps of:
 generating three arrays of bispectral data for each of three different states of the subject;
 performing statistical operations on said three arrays of bispectral data in order to identify those locations in said arrays that are significant for detecting the cerebral phenomena.

36. The system for noninvasively detecting cerebral phenomena of claim 1 further comprising:
 means for generating three arrays of bispectral data for each of three different states of the subject;
 means for statistically analyzing said arrays of bispectral data in order to identify those locations in said arrays that are significant for detecting the cerebral phenomena.

37. The method of noninvasively detecting cerebral phenomena of claim 1 wherein the cerebral phenomenon being detected is chronic ischemia or infarction in the subject being analyzed.

38. THe method of non-invasively detecting cerebral phenomena of claim 1 wherein said bispectral values are generated by computing the Fourier transform of the third order autocorrelation function of said filtered signals.

39. The method of non-invasively detecting cerebral phenomena of claim 1 wherein said bispectral values are generated by computing the Fourier transform of the third order crosscorrelation function of said filtered signals.

40. A system for noninvasively detecting cerebral phenomena comprising:
 means for acquiring electroencephalographic signals through at least one electrode from a body surface of a subject being analyzed;
 means for filtering said electroencephalographic signals to eliminate those signals having frequencies less than 2 hertz or frequencies greater than 500 hertz;
 means for dividing said filtered signals into a plurality of equally sized data records;

means for generating bispectral values capable of characterizing dynamic phase relations within said filtered electroencephalographic signals;

means for comparing said generated bispectral values to reference values in order to derive a diagnostic index that quantifies the detected cerebral phenomena.

41. The system for noninvasively detecting cerebral phenomena of claim 40 further comprising a plurality of said means for acquiring electroencephalographic signals, each of said means for acquiring electroencephalographic signals being connected to said means for filtering.

42. The system for noninvasively detecting cerebral phenomena of claim 41 wherein said plurality of said means for acquiring electroencephalographic signals is a plurality of electrodes attachable to a head of a subject being analyzed to obtain a unipolar electroencephalographic signal from each of a plurality of regions of interest on both left and right hemispheres of the subject's brain.

43. The system for noninvasively detecting cerebral phenomena of claim 40 wherein said means for acquiring encephalographic signals comprises:
  a plurality of surface electrodes for mounting on a surface of a head of the subject being analyzed;
  means for providing electrosurgery protection including a radio frequency filter for limiting radio frequency current through said electrodes;
  means for providing defibrillator protection for limiting voltage to said amplifier during a discharge;
  means for amplifying said filtered signals for a high gain in order to maximize the dynamic range for high frequency, low energy wave components of said filtered signals;
  means for feeding said signals to an analog-to-digital converter to convert said signals to digital signals.

44. The system for noninvasively detecting cerebral phenomena of claim 40 further comprising means for analyzing said signals received by each electrode in order to detect electrode failure.

45. The system for noninvasively detecting cerebral phenomena of claim 40 wherein said bispectral values are autobispectral density values and further comprising means for organizing said autobispectral density values in at least one array of autobispectral density values.

46. The system for noninvasively detecting cerebral phenomena of claim 45 where said means for generating at least one array of autobispectral density values comprises:
  means for computing fast Fourier transforms $X_i(f)$ and $Y_i(f)$ of each of said data records i;
  means for computing power spectra $P_{Xi}(f)$ and $P_{Yi}(f)$ of said data records i by squaring the magnitude of elements of said fast Fourier transforms $X_i(f)$ and $Y_i(f)$ respectively;
  means for computing for at least one electrode an average complex triple product of data records acquired by said at least one electrode;
  means for computing for said at least one electrode an average real triple product of data records acquired by said at least one electrode;
  means for computing for said at least one electrode an autobispectral density value as the absolute value of the average complex triple product for said electrode.

47. The system of noninvasively detecting cerebral phenomena of claim 46 further comprising means for computing an autobiphase value $\phi(f_1,f_2)$ for said at least one electrode such that:

$$\phi(f_1,f_2)=\tan^{-1}[\text{Im}(BC(f_1,f_2))/\text{Re}(BC(f_1,f_2))]$$

where $BC(f_1,f_2)$ is the average complex triple product for an electrode, and $f_1$ and $f_2$ designate limits of the frequency range over which the autobiphase computation is carried out.

48. The system for noninvasively detecting cerebral phenomena of claim 46 further comprising means for computing an autobicoherence value $R(f_1,f_2)$ for said at least one electrode such that $$R(f_1,f_2)=BD(f_1,f_2)/[BR(f_1,f_2)]^{\frac{1}{2}}$$

where $BD(f_1,f_2)$ is the autobispectral density value for said electrode, $BR(f_1,f_2)$ is the average real triple product for the same electrode, and $f_1$ and $f_2$ designate limits of the frequency range over which the autobicoherence computation is carried out.

49. The system for noninvasively detecting cerebral phenomena of claim 45 where said means for generating at least one array of crossbispectral density values comprises:
  means for computing fast Fourier transforms $X_i(f)$ and $Y_i(f)$ of each of said data records i;
  means for computing power spectra $P_{Xi}(f)$ and $P_{Yi}(f)$ of said data records by squaring the magnitude of elements of said fast Fourier transforms $X_i(f)$ and $Y_i(f)$ respectively;
  means for computing for at least one electrode pair an average complex triple product of all data records acquired by each of said at least one electrode pair;
  means for computing for said at least one electrode an average real triple product of all data records acquired by for each of said at least one electrode pair;
  means for computing for said at least one electrode pair a crossbispectral density value as the absolute value of the average complex triple product for said electrode pair.

50. The system for noninvasively detecting cerebral phenomena of claim 49 further comprising means for computing a crossbiphase value $\phi(f_1,f_2)$ for said at least one electrode pair such that:

$$\phi(f_1,f_2)=\tan^{-1}[\text{Im}(BC(f_1,f_2))/\text{Re}(BC(f_1,f_2))]$$

where $BC(f_1,f_2)$ is the average complex triple product for an electrode pair, and $f_1$ and $f_2$ designate limits of the frequency range over which the crossbiphase computation is carried out.

51. The system for noninvasively detecting cerebral phenomena of claim 50 further comprising means for computing an crossbicoherence value $R(f_1,f_2)$ for said at least one electrode pair such that $$R(f_1,f_2)=BD(f_1,f_2)/[BR(f_1,f_2)]^{\frac{1}{2}}$$

where $BD(f_1,f_2)$ is the crossbispectral density value for an electrode pair, $BR(f_1,f_2)$ is the average real triple product for the same electrode pair, and $f_1$ and $f_2$ designate limits of the frequency range over which the crossbicoherence computation is carried out.

52. The system for noninvasively detecting cerebral phenomena of claim 45 wherein said means for generating at least one array of autobispectral density values comprises:

means for computing autocorrelation sequences $R_{2X}(m)$ and $R_{2Y}(m)$ of all data records acquired by at least one electrode;

means for determining the orders and coefficients of parametric models for power spectra of data records acquired by said at least one electrode;

means for computing power spectra $P_X(f)$ and $P_Y(f)$ of all data records acquired by said at least one electrode;

means for computing third order moment sequences $R_{3X}(\tau)$ and $R_{3Y}(\tau)$ of data records acquired by said at least one electrode;

means for determining the orders and coefficients of parametric models of the bispectra of data records acquired by said at least one electrode;

means for computing for said at least one electrode a bispectrum of data records acquired by said at least one electrode.

53. The system for noninvasively detecting cerebral phenomena of claim 52 wherein said bispectrum is autobispectrum and further comprising means for computing an autobispectral density value for each electrode as the absolute value of the bispectrum of data records for each electrode.

54. The system for noninvasively detecting cerebral phenomena of claim 53 further comprising:

means for computing for at least one electrode a real triple product of all data records acquired by said at least one electrode;

means for computing an autobicoherence value $R(f_1,f_2)$ for said at least one electrode such that $$R(f_1,f_2) = BD(f_1,f_2)/[BR(f_1,f_2)]^{\frac{1}{2}}$$

where $BD(f_1,f_2)$ is the autobispectral density value for an electrode, $BR(f_1,f_2)$ is the real triple product for the same electrode, and $f_1$ and $f_2$ designate limits of the frequency range over which autobicoherence computation is carried out.

55. The system for noninvasively detecting cerebral phenomena of claim 53 further comprising means for computing an autobiphase value $\phi(f_1,f_2)$ for at least one electrode such that:

$$\phi(f_1,f_2) = \tan^{-1}[Im(BC(f_1,f_2))/Re(BC(f_1,f_2))]$$

where $BC(f_1,f_2)$ is the bispectrum for an electrode, and $f_1$ and $f_2$ designate limits of the frequency range over which the autobiphase computation is carried out.

56. The system for noninvasively detecting cerebral phenomena of claim 52 wherein said bispectrum is autobispectrum and further comprising means for computing an autobispectral density value for each electrode a the absolute value of the bispectrum of data records for said electrode pair.

57. The system for noninvasively detecting cerebral phenomena of claim 56 further comprising:

means for computing for at least one electrode a real triple product of all data records acquired by said at least one electrode;

means for computing a crossbicoherence value $R(f_1,f_2)$ for said at least one electrode pair such that $$R(f_1,f_2) = BD(f_1,f_2)/[BR(f_1,f_2)]^{\frac{1}{2}}$$

where $BD(f_1,f_2)$ is the crossbispectral density value for an electrode pair, $BR(f_1,f_2)$ is the real triple product for the same electrode pair, and $f_1$ and $f_2$ designate limits of the frequency range over which the crossbicoherence computation is carried out.

58. The system for noninvasively detecting cerebral phenomena of claim 53 further comprising means for computing a crossbiphase value $\phi(f_1,f_2)$ for at least one electrode pair such that:

$$\phi(f_1,f_2) = \tan^{-1}[Im(BC(f_1,f_2))/Re(BC(f_1,f_2))]$$

where $BC(f_1,f_2)$ is the crossbispectrum for an electrode pair, and $f_1$ and $f_2$ designate limits of the frequency range over which the crossbiphase computation is carried out.

59. The system for noninvasively detecting cerebral phenomena of claim 40 wherein said bispectral values are autobicoherence variables and further comprising means for organizing said autobicoherence values in at least one array of autobicoherence values.

60. The system for noninvasively detecting cerebral phenomena of claim 40 wherein said bispectral values are autobiphase values and further comprising means for organizing said autobiphase values in at least one array of autobiphase values.

61. The system for noninvasively detecting cerebral phenomena of claim 40 wherein said bispectral values are crossbispectral density values and further comprising means for organizing said crossbispectral density values in at least one array of crossbispectral density values.

62. The system for noninvasively detecting cerebral phenomena of claim 40 wherein said bispectral values are crossbicoherence values and further comprising means for organizing said crossbicoherence values in at least one array of autobicoherence values.

63. The system for noninvasively detecting cerebral phenomena of claim 40 wherein said bispectral variables are crossbiphase values and further comprising means for organizing said crossbiphase values in at least one array of autobiphase values.

64. The system for noninvasively detecting cerebral phenomena of claim 40 wherein said means for acquiring encephalographic signals further comprises means for obtaining bipolar data sets of electroencephalographic signals from different regions of a brain of said subject.

65. The system for noninvasively detecting cerebral phenomena of claim 40 wherein said means for comparing further comprises:

means for organizing said generated bispectral values in an array of bispectral variables;

means for selecting a physical phenomena to be diagnosed;

means for retrieving an appropriate bispectral reference array from a resident memory, said reference array containing frequency pairs that are most sensitive to the physical phenomena to be diagnosed;

means for adding data values in locations of each of said at least one array of bispectral values that are identified by the retrieved reference array as being locations containing data of significance to obtain a sum of said significant locations;

means for averaging the values stored in said significant locations to generate a diagnostic index relating to the cerebral phenomena to be detected.

66. The system for noninvasively detecting cerebral phenomena of claim 40 further comprising:

means for generating three arrays of bispectral data for each of three different states of the subject;

means for performing a paired Student's t test comparing the data in a first and a second array of said three arrays of bispectral data to produce a first t array and performing a paired Student's t test comparing the data in said second and a third array of said three arrays of bispectral data to produce a second t array;

means for comparing each data value in said first t array with data values in corresponding locations in said second t array;

means for identifying those corresponding locations in said first and second t arrays that differ by more than a preselected amount, said identified locations representing those locations that are significant for detecting the cerebral phenomena.

67. The system for noninvasively detecting cerebral phenomena of claim 40 further comprising means for displaying a representation of a subject's head, divided into a selected number of sections, said means for displaying including means for displaying a compressed continuous tracing of a computer diagnostic index determined from the signals acquired from an electrode positioned at a location represented by said section.

68. The system for noninvasively detecting cerebral phenomena of claim 64 wherein each displayed section includes a background of one of a plurality of colors, each of which colors is unique to a distinct selected range of possible values of a selected diagnostic index.

69. The system for noninvasively detecting cerebral phenomena of claim 40 wherein said means for generating bispectral values comprises a means for computing the Fourier transform of the third order autocorrelation function of said filtered signals.

70. The system for noninvasively detecting cerebral phenomena of claim 40 wherein said means for generating bispectral values comprises a means for computing the Fourier transform of the third order crosscorrelation function of said filtered signals.

* * * * *